(12) United States Patent
Anzalone

(10) Patent No.: US 6,180,658 B1
(45) Date of Patent: Jan. 30, 2001

(54) METHOD FOR COUNTERACTING BLOOD PLATELET AGGREGATION IN A PATIENT IN NEED THEREOF

(75) Inventor: Sergio Anzalone, Rome (IT)

(73) Assignee: Medosan Ricerca S.r.l., Rome (IT)

( * ) Notice: Under 35 U.S.C. 154(b), the term of this patent shall be extended for 0 days.

(21) Appl. No.: 09/182,312

(22) Filed: Oct. 30, 1998

Related U.S. Application Data

(63) Continuation-in-part of application No. 08/906,976, filed on Aug. 6, 1997, now Pat. No. 5,889,041, which is a continuation-in-part of application No. 08/679,807, filed on Jul. 15, 1996, now Pat. No. 5,866,600.

(30) Foreign Application Priority Data

Jul. 14, 1995 (IT) .............................................. RM95A0484

(51) Int. Cl.[7] .................................................. A61K 31/40

(52) U.S. Cl. ........................................... 514/423; 514/428

(58) Field of Search ...................................... 514/423, 428

(56) References Cited

U.S. PATENT DOCUMENTS

| | | | |
|---|---|---|---|
| 4,578,481 | 3/1986 | Baglioni | 548/539 |
| 4,882,349 | 11/1989 | Baglioni | 514/423 |
| 5,478,481 | 12/1995 | Kazama et al. | |

FOREIGN PATENT DOCUMENTS 0 755 679   1/1997   (EP) .

OTHER PUBLICATIONS

E. Tubaro et al, "Studies on the gastric tolerability of the new non–sterodidal anti–inflammatory drug amtolmetin guacyl", Arzneimittelforschung, vol. 45 No. 12, pp. 1298–1302, Dec. 1995.

A. Caruso et al, "Pharmacological properties and toxicology of MED–15, a prodrug of tolmetin", Drugs under Experimental and Clinical Research, vol. 18, No. 11/12, pp. 481–485 No Date of Publication.

Dialog File Supplier: File 129: PHIND; AN=560550; SCRIP 2290, p. 9, XP002061890, 1997.

M. Delfino, et al, "Evaluation of the Therapeutic Activity and Gastrolesive Effects of a New NSAID vs Placebo in Patients with Osteroarticular Diseases"; Clin Ter., 147:3, pp. 113–116, XP002061891.

M. Lingetti et al, An Evaluation of the Therapeutic Activity of ST–679 in Patients with Osteoarthritis at Different Sites, Clin. Ter., 142:1, p. 2, 1993, No Date of Publication.

G. Donati et al, "A Clinical Study Intended to Establish the Optimum Dosage of St–679 in Rheumatic Disorders", Clin Ter., 142:1, pp. 19–28, 1993.

*Primary Examiner*—Gary Geist
*Assistant Examiner*—Everett White
(74) *Attorney, Agent, or Firm*—Browdy and Neimark

(57) ABSTRACT

The present invention relates to A method for counteracting blood platelet aggregation in a patient in need thereof and in need of a treatment of pain and inflammation, comprising administering (on an empty stomach) an amount of 2-methoxyphenyl-1-methyl-5p-methylbenzoyl-pyrrol-2-acetamido acetate effective to treat pain and inflammation and to avoid platelet aggregation.

The present invention relates further to a method for treating trombophlebitis and pain and inflammation in an infarct patient or in a patient suffering by or under risk of cerebral stroke of thrombotic origin comprising administering on empty stomach an anti-inflammatory effective amount of 2-methoxyphenyl-1-methyl-5p-methylbenzoyl-pyrrol-2-acetamido acetate (known also as amtolmetin guacyl and indicated in the present description also as MED 15).

14 Claims, 19 Drawing Sheets

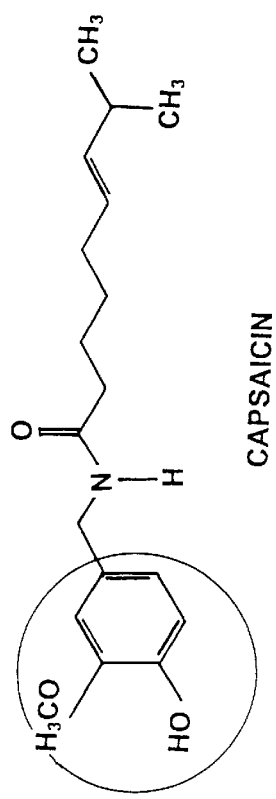
CAPSAICIN
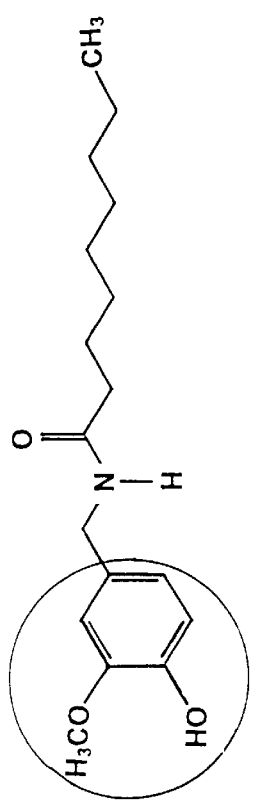
NONANOYL VANILLYLAMIDE
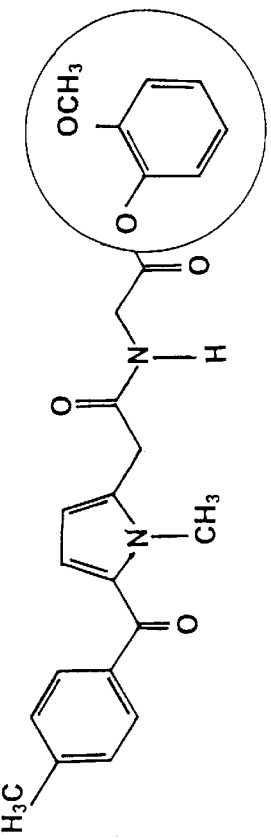
MED 15
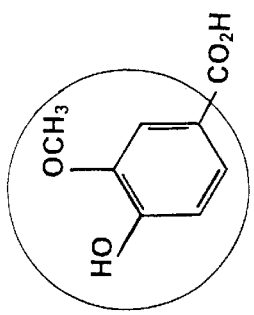
VANILLIC ACID
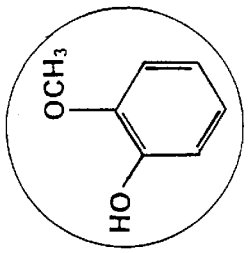
GUAICOL
FIG.15

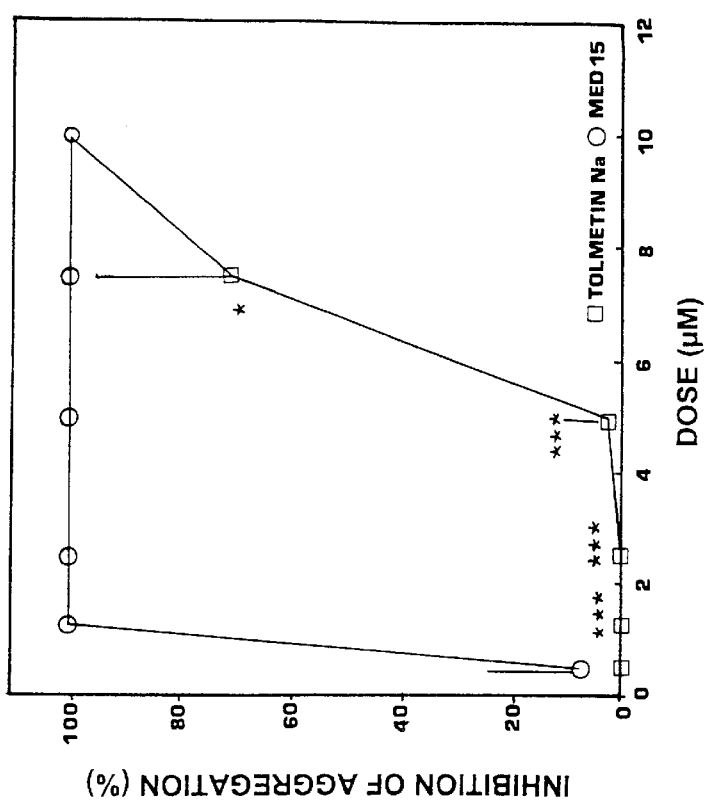
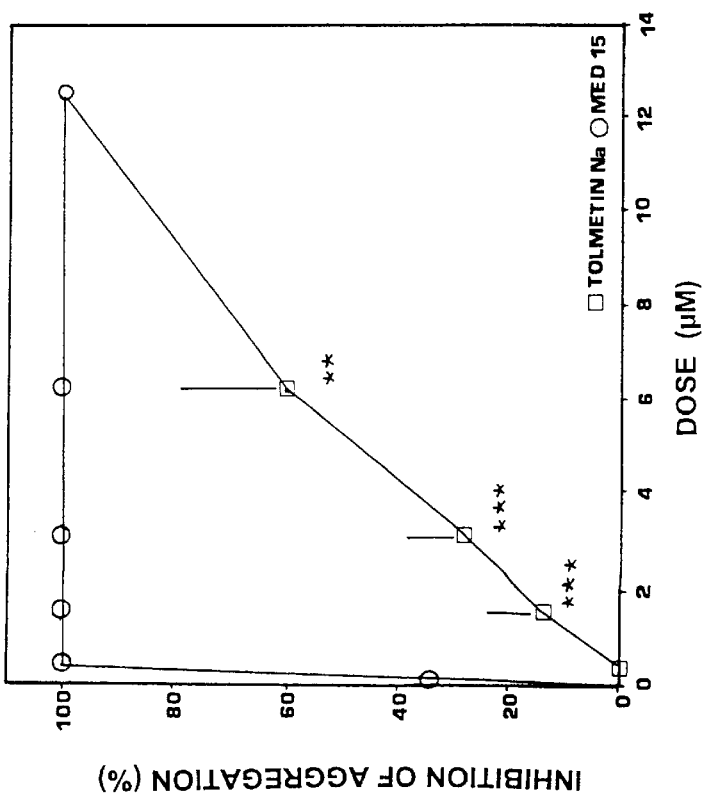
EFFECT OF MED 15 AND TOLMETIN ON PLATELET AGGREGATION
IN VITRO STUDY RABBIT PLATELETS
FIG. 19

METHOD FOR COUNTERACTING BLOOD PLATELET AGGREGATION IN A PATIENT IN NEED THEREOF

This is a continuation-in-part of application Ser. No.08/906,976 filed on Aug. 6, 1997 is now U.S. Pat. No. 5,889,041. Which is a Continuation-in-Part of 08/679,807 filed Jul. 15, 1996 now U.S. Pat. No. 5,866,600.

The present invention relates to a method for treating an inflammatory pathological condition in a patient in need thereof, comprising administering on empty stomach an anti-inflammatory effective amount of 2-methoxyphenyl-1-methyl-5p-methylbenzoyl-pyrrol-2-acetamido acetate (known also as amtolmetin guacyl and indicated in the present description also as MED 15).

BACKGROUND ART

Non-steroidal anti-inflammatory drugs (NSAIDs) . have been used for many years in therapy. It is also well known that NSAIDs produce lesions to gastrointestinal apparatus depending on the length of the treatment and on the type of drug. This problem has a dramatic importance in cases where the therapy must be protracted for a long time. An example is rheumatoid arthritis in old people, where a chronic treatment is needed to keep under control the inflammatory state and the pain and make acceptable the quality of life.

At present there is a pharmacological dogma establishing a mandatory connection between anti-inflammatory effect and gastric lesions. This dogma has been recently shaken by the availability of newly synthesised anti-inflammatory drugs showing gastrolesive effects lower than those of old ones. Notwithstanding that equiactive doses of drug could produce lesions of different seriousness, it was settled that an anti-inflammatory drug showed, in any case, a gastrolesive effect. From this fact it followed that it could not be expected that these drugs known in the art could show a gastroprotective effect.

It is also well known, and this has a pharmacological relevance too, that the administration of NSAIDs reflects negatively on renal function, in particular by provoking a remarkable decrease in diuresis. This effect is due to prostaglandin blockade; in fact, prostaglandin physiologically dilate the renal vascular system. The blocking effects of traditional NSAIDs lead to vasoconstriction and to the consequent inhibition of diuresis. From this fact it followed that it could not be expected that these drugs known in the art could be administered without negatively affecting the renal function.

Even more so in view of the above, it could not be expected that a NSAID could simultaneously show a gastroprotective effect without negatively affecting the renal function while at the same time maintaining a high anti-inflammatory activity.

It is also well known that in view of their side-effects on gastric mucosa, NSAIDs are invariably administered after meals or, in general, when the stomach is not empty. The generality of this pharmacological principle finds a practical confirmation in the recommendations found in the packagings of the drugs in commerce. Basically the idea is that the effects of the hypersecretion of hydrochloric acid provoked by the administration of NSAIDs may be, at least partially, counteracted by the presence of food.

It has been now surprisingly found that the compound 2-methoxyphenyl-1-methyl-5p-methylbenzoyl-pyrrol-2-acetamido acetate, which is an effective anti-inflammatory non-steroidal drug as already known in the art, shows a remarkable atisecretory activity on gastric secretion in mammals without affecting the renal function, but, on the contrary, increasing the diuresis. This increase in diuresis is linked to its mechanism of action; in fact, the overflow of neuropeptides (in particular CGRP) produced in the stomach by MED 15 and flowing from the stomach into the bloodstream, produces renal capillary vasodilatation, with reversal of its effect on prostaglandin.

Additionally, and more than unexpectedly for a NSAID, it has been found that amtolmetin guacyl, in order to show its efficacy (gastroprotection and renal tolerability together with an anti-inflammatory effect unchanged), has to be administered on empty stomach in view of the peculiarity of its action mechanism.

The compound 2-methoxyphenyl-1-methyl-5p-methylbenzoyl-pyrrol-2-acetamido acetate is already known in the art and is for instance disclosed in Italian patent application no. 47881A/82 and in U.S. Pat. No. 4,578,481 issued on Mar. 25, 1986.

Both the documents of the state of the art disclose that the above compound shows anti-inflammatory, analgesic, antipyretic, antitussive and antisecretive (on the mucus of the respiratory airway) properties. No mention, either direct or indirect, is made about a possible antisecretive effect on the gastric secretion in mammals.

It is therefore the subject matter of the present invention a method for treating an inflammatory pathological condition in a patient in need thereof, comprising administering on empty stomach an anti-inflammatory effective amount of 2-methoxyphenyl-1-methyl-5p-methylbenzoyl-pyrrol-2-acetamido acetate.

BRIEF DESCRIPTION OF THE DRAWINGS

With the present description are enclosed eighteen sheets of drawings in which:

FIG. 15 shows a comparison among the molecular structures of capsaicin, nonanoyl vanillylamide and amtolmetin guacyl;

FIG. 19 shows the effect of MED 15 and Tolmetin on platelet aggregation in two graphs of experiments using as agonists collagen (19a) and arachidonic acid (19b).

CHEMISTRY

Figure 1:
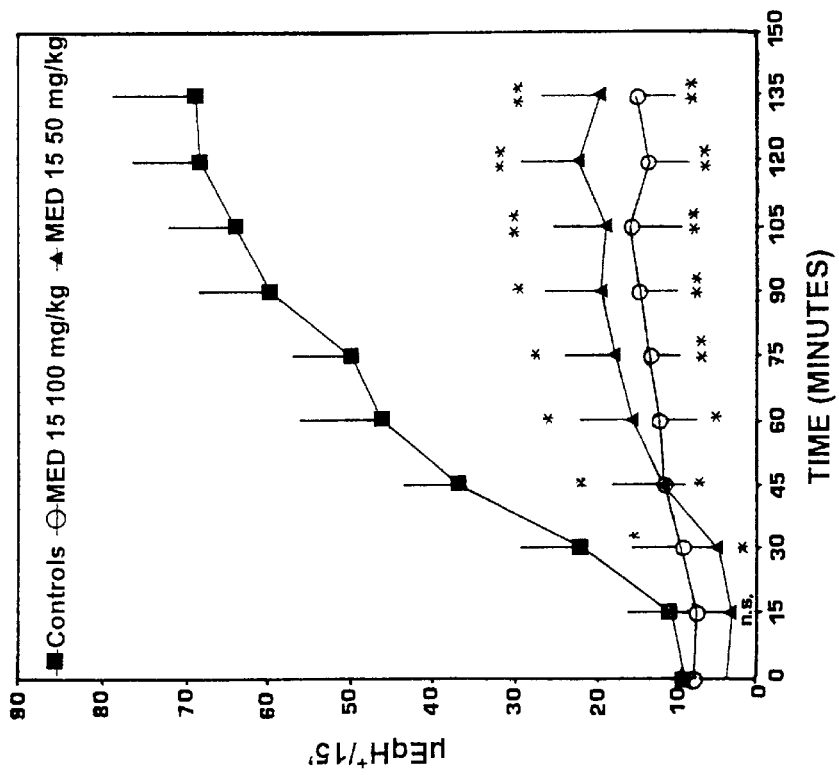
FIGS. 1, 2, 3 and 4 show the "in vivo" effect of amtolmetin guacyl on gastric acid secretion of the rat, using as an agonist histamine, carbachol, gastrin and peptone, respectively.
Figure 2:
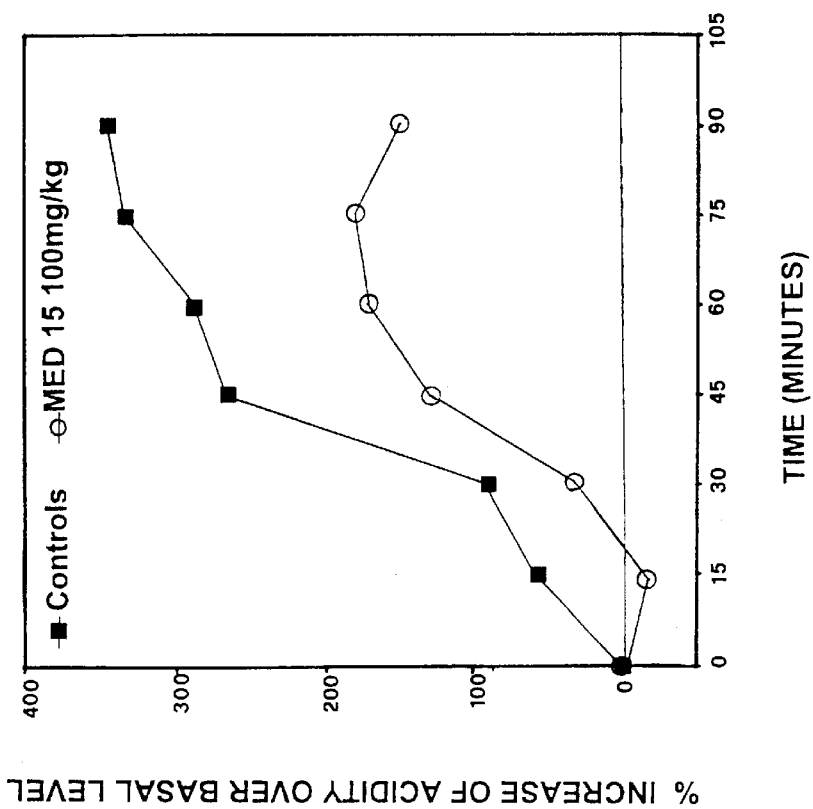
Figure 3:
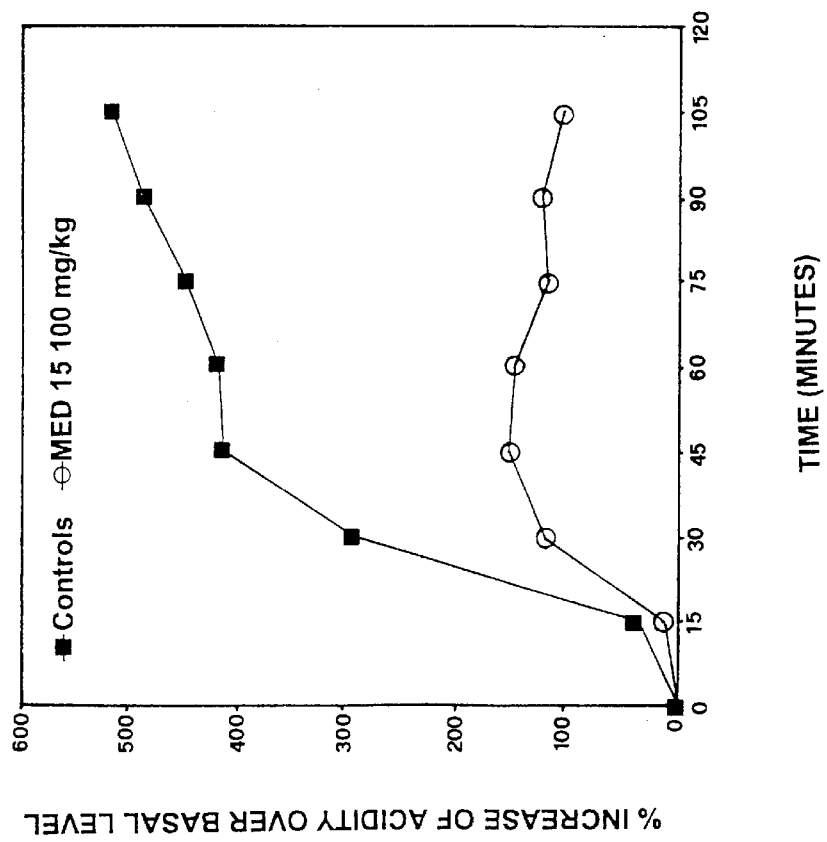
Figure 4:
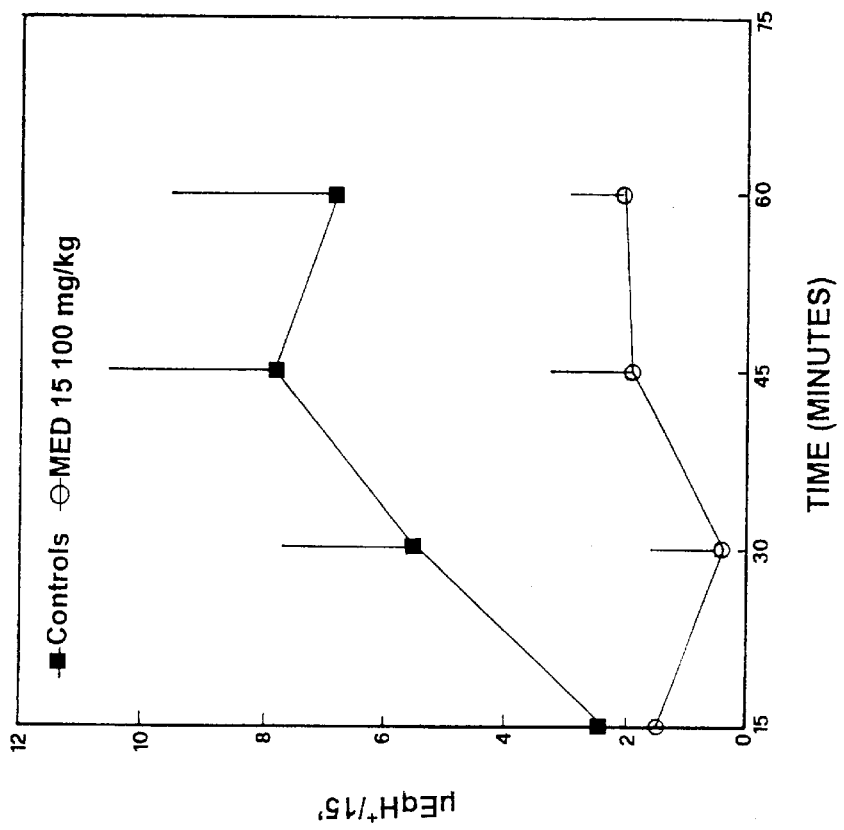

The molecule of amtolmetin guacyl was synthesised using modern chemical technology now known as "Combinatorial Chemistry". This neologism was coined in the United States as recently as 1993, but the technique was known years before. This new synthetic chemistry technique consists in combining molecular species bioactive in themselves, to obtain molecules which possess pharmacological properties totally different from those of the single starting components. Traditionally, a staring molecule was manipulated through the substitution of a number of radicals, now the procedure is less random and starts from molecular moieties which are pharmacologically active per se (Combinatorial Chemistry, Editorial Feb. 12, 1996, C&EN) . The amtolmetin guacyl molecule was born this way, producing a drug with completely new characteristics, totally different from the bioactivity of the various moieties.

While the production and characterisation of the compound amtolmetin guacyl are disclosed in the above mentioned US and Italian documents which are hereby incorporated for reference, in the following 1) the results of pharmacological tests showing the antisecretive activity and 2) the pharmacotoxicological profile and 3) the mechanism of action of the above compound and 4) clinics are reported.

1) Pharmacological tests showing the antisecretive activity on animals.

Chemicals and Animals used

The following substances have been used: carboxymethylcellulose sodium, histamine dichloride, piroxicam, carrageenin and acetylcholine chloride produced by Sigma Chimica (Milano, Italy); cimetidine produced by Farchemia (Milano, Italy); 2-methoxyphenyl-1-methyl-5p-methylbenzoyl-pyrrol-2-acetamido acetate and naproxen produced by Alfa Chemicals Italiana (Bergamo, Italia); diclofenac sodium, nimesulide and tolmetin produced by LCM Trading (Milano, Italy); gastrin produced by Fluka Chimica (Milano, Italy). Male Wistar rats, 250±10 g b.w. (Charles River, Calco, Como, Italy), quarantined for five days prior to the beginning of the trial and divided into groups of 3 animals per cage, were used for determination of gastric lesions and of $ID_{50}$ determination. Immature male Wistar rats, 30–45 g b.w. (Harlan Nossan, Milano) were used for the determination of the antisecretory effect on isolated rat stomach. The guinea-pigs used were the Dunkin Hartley guinea-pigs (Harlan Nossan, Milano, Italy).

The animals were fed standard laboratory chow with free access to water under animal house conditions of 22±2° C. temperature, relative humidity 55±10% and 12-h light-dark cycle..

Determination of Gastric Lesions

In this first test the effect of the compound 2-methoxyphenyl-1-methyl-5p-methylbenzoyl-pyrrol-2-acetamido acetate and of some reference NSAIDs (diclofenac sodium, naproxene, nimesulide, piroxicam and tolmetin) on the gastric mucosa of rat after repeated oral administration in order to test the existence and extent of the gastric lesions, has been verified.

The animals entered in the trial, randomized and divide into groups of 6 rats each, were fasted for 16 h prior to treatment, with access to water ad libitum. They were re-fed 1 h after drug administration. The compound 2-methoxyphenyl-1-methyl-5p-methylbenzoyl-pyrrol-2-acetamido acetate and the other reference NSAIDs, suspended in 1% carboxymethylcellulose (CMC) solution, were orally administered by gastric gavage in a volume of 6 ml/kg for four consecutive days. Controls received the vehicle in the same way as the treated animals. 4 h after the last administration the animals were killed by ether overdose; the stomachs were removed, rinsed with 10 ml of saline and immersed in 1% formalin. They were later opened along the greater curvature and the mucosa examined for lesions.

The seriousness of the lesion was quantified according to a scale graduated from 1 to 3 according to the size of the lesions: 1=ulcer<1 mm; 2=ulcer 1–2mm; 3=ulcer>2mm. The total sum was divided by 10 to obtain the "erosion index". The gastric lesions were evaluated by two independent investigators under blind conditions according to Main & Whittle method (BJ Pharmac 1975:53; p. 217–224).

Since pharmacological studies in carrageenin-induced paw oedema in rat show that a daily 50mg/kg dose in oral administration of 2-methoxyphenyl-1-methyl-5p-methylbenzoyl-pyrrol-2-acetamido acetate is higly-efficacious as anti-inflammatory agent, this daily dose has been selected for the evaluation of the gastric lesions of same compound. Since the average daily dose in man (for the anti-inflammatory activity) is 600 mg, the comparative efficacious dose in the rat is in the ratio of 12:1. More precisely, comparative evaluation with the other NSAID compounds was calculated as follows:

600 mg/die: 50 mg/kg=daily dose of reference NSAID in man: X where X represents the daily dose of the reference NSAID in rat. This criterion keeps into account the "real" activity ratio in man. In this work the "ratio to rat dosage" has also been included which keeps into account ratios homogeneous to the same animal species. To evaluate the "ratio to rat dosage" the $ID_{50}$ has been determined using the carrageenin-induced oedema as inflammatory test. This made possible to determine in rat an equiactive dose which is, consequently, comparable among the various compared NSAIDs.

Determination of $ID_{50}$ $ID_{50}$. relative to the products under examination (considered in table 1), has been evaluated using the anti-inflammatory response to carrageenin-induced paw oedema (according to Wong et al, J Pharmacol Exp, 1973–1855; pages 127–138). The products, suspended in 1% CMC, were administered orally in a total volume of 5 ml/rat. 1 h later, 0.1 ml of 1% carrageenin sterile solution was injected into the hind subplantar aponeurosis. Volume of the paw was measured immediately prior to injection of the phlogogen and 2 h thereafter, by means of a plethysmograph. The percentage of inhibition of oedema was calculated as follows:

$$1 - \Delta V \text{ treated}/\Delta V \text{ control} \times 100$$

where $\Delta V$=final V−initial V.

Three doses have been used for each NSAID and the $ID_{50}$, which indicates the quantity in mg/kg inhibiting oedema by 50%, has been determined.

The results are listed in the following table 1, where each expressed value is the average of 6 determinations. In this table the results either of the so-called "ratio to human dosage" and of the "ratio to rat dosage" are listed.

TABLE 1

Comparison of the effects of amtolmetin guacyl and reference compounds on the rat gastric mucosa following repeated oral administration

| DRUG | Ratio to human dosage (mg/kg) | Gastro-lesive index | Ratio to rat dosage (mg/kg) (ID$_{50}$ mg/kg ×5) | Gastro-lesive index |
|---|---|---|---|---|
| Controls | — | 1.0 | — | 1.0 |
| amtolmetin guacyl | 50.0 | 1.0 | 100 | 1.0 |
| Diclofenac sodium | 7.5 | 68.1[a] | 15.8 | 63.7 |
| Naproxen | 37.5[b] | 273.8[c] | 34.0 | 283.7 |
| Nimesulide | 16.6 | 21.3 | 28.5 | 46.2 |
| Piroxicam | 2.0 | 31.3 | 13.8 | 176.2 |
| Tolmetin[d] | — | — | 61.2[d] | 79.7 |

Each value is the mean of 6 rats.

a) Diffuse haemorrhagic gastritis was also present b) Naproxen was taken at the lowest dosage used in man (450 mg/day)

c) One animal died after the third treatment and two showed extremely thin stomach walls d) Tolmetin was administered at an equimolar dose compared to amtolmetin guacyl In order to exacerbate possible side effects on the stomach the dosage of amtolmetin guacyl was quadruplicated. Results are reported in Table 2.

TABLE 2

Effects of a high dosage of amtolmetin guacyl compared to controls

| Groups | Dose (mg/kg) | Rats with lesions/rats used | Erosion index | Gastrolesive index |
|---|---|---|---|---|
| Controls | — | 2/6 | 0.066 | 1.0 |
| MED15 | 200 | 2/6 | 0.066 | 1.0 |

MED15 200 2/6 0.066 1.0

MED15 (amtolmetin guacyl) was administered for 4 consecutive days by oral gavage In order to obtain a histological evaluation of the results obtained in our laboratories, an independent laboratory was provided with identical samples of the material evaluated by us, under totally blind conditions.

TABLE 3

Observation of mucosal lesions in intact stomach

| Nr | Drug | Microscopic findings | Macroscopic findings | Histology |
|---|---|---|---|---|
| 2 | MED15 | 0 | 0 | no histological lesions |
| 3 |  | 0 | 0 | no histological lesions |
| 4 |  | 0 | 0 | no histological lesions |
| 5 | Diclofenac | 2* | 2 | *multiple areas of |
| 6 |  | 3* | 4 | necrotic mucosal |
| 7 |  | 9* | 7 | ulceration extending through the gastric foveola, not involving |
| 8 | Tolmetin | 2+ | 3 | the glandular region +small, superficial necrotic ulcers |
| 9 |  | 0+ | 0 |  |
| 10 |  | 1+ | 0 | extending through the gastric foveola, not involving the intrafoveolar stroma |

Rats were treated with amtolmetin guacyl by oral gavage (50 mg/kg); diclofenac (7.5 mg/kg); tolmetin (66.6 mg/kg).

Histological evaluation of the state of the mucosa of variously-treated rats are reported in Table 4.

TABLE 4

Histological effect of repeated administration of MED15 (amtolmetin guacyl) and reference compounds (ratio to rat dosage)

| Animal n. | Drug | Macroscopic findings | Histology |
|---|---|---|---|
| 1 | Tolmetin | ulcer of the corpus | 1–3 mm areas of coagulative necrosis involving entire mucosal thickness |
| 4 |  | 2 ulcers of the corpus | 1–3 mm areas of coagulative necrosis involving entire mucosal thickness |
| 3 |  | 8 small ulcers | >1 mm areas of cellular necrosis extending through two-thirds of the mucosa (surface epithelium, region of mucous neck cells and of parietal cells) |
| 5 |  | multiple dark lesions | >1 mm areas of cellular necrosis extending through two-thirds of the mucosa (surface epithelium, region of mucous neck cells and of parietal cells) |
| 2,6 |  | normal | no histological lesions |
| 7,8,9, 10,11, 12 | MED15 | normal | no histological lesions |
| 13 | Controls | normal | 2 areas of necrosis <1 mm diameter involving entire mucosal thickness no histological lesions |
| 14,15 |  | normal | no histological lesions |
| 16,17 | Diclofenac | multiple tiny ulcers | 2 areas of coagulative necrosis involving entire mucosal thickness |
| 18,19 |  | mucosal ulcers | multiple areas of coagulative necrosis extending through two thirds of the mucosa |
| 20,21 |  | normal | no histological lesions |

Rats were treated with amtolmetin guacyl by oral gavage (100 mg/kg), diclofenac (15.8 mg/kg) and tolmetin (61.2 mg/kg) in CMC 1% for 4 consecutive days. Controls received the vehicle only, also by oral gavage. 4 h after the final administration the animals were killed by ether overdose and the stomachs removed, rinsed in saline and immersed in formalin 4%.

The histological results confirmed what we had previously seen wits the dissection microscope; the difference between amtolmetin guacyl and the other NSAIDs appeared enormous. In particular, it was emphasized the better aspect of the gastric mucosa of some of the stomachs (which were revealed to be those of amtolmetin guacyl and had also been observed in our laboratories) (b.r. No.17). This difference between amtolmetin guacyl and the controls piloted us towards research of possible gastro-protective effects of the molecule. The question posed was whether the product in some way influenced the gastric acid secretion which is well known to be at the basis of NSAID-induced gastric damage.

Antisecretive activity in vitro in the rat At the beginning, the isolated, perfused, immature rat stomach, treated externally with the study product, was used. We preferred to use the isolated stomach in toto rather than strips (B.R. No. 18, 19 and 20) in order not to exclude a section of the stomach (the antrum), unimportant for acid secretion but very important for the secretion of bicarbonates and bioactive peptides (b.r. No. 21, 22). The results were encouraging, since amtolmetin guacyl inhibited acid production stimulated by the three classic agonists (histamine, acetilcholine and gastrin) both using varying doses of agonist or varying doses of amtolmetin guacyl (Table 5).

The results are listed in the following table 6.

TABLE 6

Antisecretory activity of amtolmetin guacyl in rat

| Time (min) | amtolmetin guacyl 50 mg/kg $\mu EqH^+/15'$ | P $\leq$ | amtolmetin guacyl 100 mg/kg $\mu EqH^+/15'$ | P $\leq$ | Controls $\mu EqH^+/15'$ |
|---|---|---|---|---|---|
| 0 | 4 | — | 8 | — | 9 |
| 15 | 4 | n.s. | 7 | n.s. | 12 |
| 30 | 5 | 0.05 | 9 | 0.05 | 22 |
| 45 | 11 | 0.05 | 11 | 0.05 | 36 |
| 60 | 15 | 0.05 | 12 | 0.05 | 46 |
| 75 | 17 | 0.05 | 13 | 0.01 | 50 |
| 90 | 19 | 0.05 | 14 | 0.01 | 60 |
| 105 | 18.5 | 0.01 | 15 | 0.01 | 63 |
| 120 | 22 | 0.01 | 13 | 0.01 | 68 |
| 135 | 20 | 0.01 | 14 | 0.01 | 69 |

In all other experiments gastric acid secretion was stimulated with carbachol, gastrin and peptone and the results were perfectly coherent.

TABLE 5

Effect of MED15 (amtolmetin guacyl) on gastric secretion of the rat in vitro

| n. anims. | Agonist (M) | Δacid (nmol/min) | n° anims. | Antagonist (M) | Δacid (nmol/min) | % inhib. | P |
|---|---|---|---|---|---|---|---|
| 23 | Histamine $10^{-4}$ | 51.3 ± 6.4 | 11 | MED15 $10^{-4}$ | 19.2 ± 5.4 | 62.6 | 0.003 |
| | | | 6 | MED15 $10^{-5}$ | 16.1 ± 5.4 | 68.7 | 0.010 |
| 7 | Histamine $10^{-3}$ | 42.3 ± 4.9 | 5 | MED15 $10^{-4}$ | 17.9 ± 2.1 | 57.7 | 0.003 |
| 8 | Histamine $10^{-4}$ | 67.0 ± 17.8 | 5 | Cimetidine $10^{-4}$ | 14.3 ± 7.2 | 78.6 | 0.047 |
| 6 | Acetylcholine $10^{-3}$ | 90.2 ± 6.5 | 6 | MED15 $10^{-4}$ | 71.2 ± 5.4 | 21.5 | 0.050 |
| 10 | Gastrin $6 \times 10^{-7}$ | 64.0 ± 5.6 | 6 | MED15 $10^{-4}$ | 30.7 ± 3.7 | 52.1 | 0.0001 |

The results are expressed as mean±S.E.

The comparison with cimetidine, known antiulcer drug, with similar values is a further confirmation of the effectiveness of the antisecretory activity of amtolmetin guacyl.

Antisecretory activity in vivo in rat At this point we wished to confirm these results in vivo in a stomach model (b.r. No. 23), maintaining all of nervous and vascular connections intact.

The methods used were those described by G Coruzzi, M. Adami, C. Pozzoli, E. Poli, G. Bertaccini (Pharmacology .1994;48: pages 69–76) and M. Leitold, W. Fleissig and A. Merk (Arzneim-Forsch/Drug Res. 34(I), Nr. 4, 1984).

The animals were treated in oral administration with amtolmetin guacyl 50 or 100 mg/kg, 1 h before the beginning of the perfusion with histamine. The controls received only the vehicle (CMC 1% ).

After anaesthesia with urethan (1.25 g/kg i.p.), the oesophagus was ligated close to the stomach. Two cannulas of polyethylene are then inserted: one was inserted in the forestomach, the second one was inserted directly into the pyloric sphincter. The stomach was flushed with saline at 37° C. (1 ml/min) and the flushed liquid, collected every 15 minutes, titred at ph 7 with NaOH $10^2$ M. The acid secretion was induced by an intravenous infusion (0.1 ml/min) of histamine (30 $\mu$mol/kg/h).

The acidity is expressed as $\mu EqH^+/15$ min.

All of our results, both with the isolated stomach and with the stomach in situ, were duplicated and confirmed by the Huntingdon laboratories in the U.K. (b.r. No. 24, 25). Although these works are not available to the public at the filing date of the present application, they confirm the findings of the Applicant's tests and may be inspected with consent of Applicant.

2) Pharmaco-toxicological profile
Anti-inflammatory activity
Amtolmetin guacyl as an anti-inflammatory agent as confirmed by the pharmacological studies
Moreover, as with all the NSAIDs currently aveilable, it inhibits gastric $PGE_2$ in the rat, albeit to a lesser degree than ASA (Table 7).

TABLE 7

Effect of MED15 and of ASA* on gastric $PGE_2$ in the rat

| Groups | $PGE_2$ (ngtg$^\Delta$ tissue) ± S.E. | % inhibition | P |
|---|---|---|---|
| Controls | 108.7 ± 23.9 | | |
| MED15 | 32.7 ± 8.5 | 69.9 | 0.022 |
| ASA | 14.4 ± 4.5 | 86.7 | 0.003 |

(*) = acetyl salicylic acid
(Δ) = nanograms for grain of tissue

In order to have a full evaluation of the anti-inflammatory activity of the amtolmetin guacyl, a number of experimental tests have been carried out to duplicate the results already available to the Applicant. The tests have been carried out by the William Harvey Institute as follows.

Carrageenan Pleurisy

Methods

Dosing

Compounds were administered orally 1 hour prior to and 1 hour post pleurisy induction in a volume of 0.5 ml 1% gum tragacanth. Indomethacin was used at 3 mg/kg. MED 15 was used at 25, 50 and 100 mg/kg.

Preparation of carrageenan

A 1% solution of carrageenan in sterile saline was prepared. The solution was placed in an incubator at 37° C. for half an hour to allow complete hydration of the carrageenan. The solution was then mixed to homogeneity.

Induction

A 21G×40 mm syringe needle was reduced in length to 5 mm and fitted to a 1 ml syringe containing the irritant. Rats were lightly anaesthetised with halothane. Each animal was placed on its left side. The skin over the thorax was lifted with and a 1 cm incision made through the skin with a pair of scissors. The wound was opened to expose the underlying muscle. Using a scalpel, a 2–3 mm incision was made into the muscle of the 5th–6th intercostal space. A volume of 0.15 ml of carrageenan solution was then injected into the pleural cavity. The wound was closed with a 11 mm Michel clip and the animal allowed to recover from the anaesthetic. Groups of animals were killed 4 hours after pleurisy induction.

Collection of pleural exudate

Lavage solution: One part of 3.15% trisodium citrate solution, mixed with nine parts of Hank's balanced salt solution.

Rats were killed by over exposure to carbon dioxide. For each rat the skin over the thorax was moistened with IMS alcohol. The skin over the sternum was then lifted and a 5 cm cut made, to expose the musculature of the upper abdomen and thoracic cavity. The muscle overlying the xiphisternum was lifted with tissue forceps and a 1 cm cut made through the muscle to reveal the cartilage. This was then lifted and the diaphragm perforated just beneath the cartilage. Two cuts were then made through the rib cage either side of the cartilage to form a flap which could be folded back to expose the thoracic cavity.

Using a syringe, 1 ml of lavage fluid was introduced into the thoracic cavity. The fluid was aspirated 2–3 times with a 3 ml pastette to wash the cavity, before being collected into separate 10 ml conical-based plastic test-tubes. Any blood contaminated fluids were rejected.

Quantification of Exudates

The mass of each tube with fluid was determined. By subtracting the mass of an empty tube from these values, and assuming a density for the fluid of 1 $g/cm^3$; the fluid volume was quantified.

Statistical Analysis

Results were analysed by ANOVA followed by Bonferroni T-test. Values of $p<0.05$ were considered significant.

RESULTS

Results for exudated volume are shown in Table 8. Dosing was one hour prior to and one hour post pleurisy induction and inflammation was assessed at 4 hours.

Exudate volume

Exudate volume for gum tragacanth control was 0.94±0.04 ml. Indomethacin at 3 mg/kg caused a 50% reduction in exudate volume ($p<0.01$) compared to gum tragacanth control. MED 15 at all concentrations tended to decrease exudate volume by 11%, 21% and 44% at 25, 50 and 100mg/kg respectively; with the highest dose giving a statistically significant reduction ($p<0.05$) compared to gum tragacanth control.

TABLE 8

Carrageenan pleurisy (4 hour)

| | Control (gum tragacanth) (n = 10) | Indomethacin 3 mg/kg (n = 11) | MED 15 25 mg/kg (n = 9) | MED 15 50 mg/kg (n = 10) | MED 15 100 mg/kg (n = 9) |
|---|---|---|---|---|---|
| Exudate volume (ml) | 0.94 ± 0.04 | 0.47 ± 0.11 P < 0.01 | 0.84 + 0.09 p = NS | 0.74 ± 0.06 p = NS | 0.53 ± 0.05 P < 0.05 |

Adjuvant Arthritis

Methods

Dosing

The drugs were administered daily by oral gavage for 4 days (day 0–3); piroxicam and MED 15 were dissolved in 5% Gum arabic+0.01% Tween 80, and administered in a volume of 0.5 ml. Piroxicam was administered as 3 mg/kg and MED 15 was administered as 25, 50 and 100 mg/kg doses.

TABLE 8 bis illustrating dosage regimes.
L = left stifle joint, R = Right stifle joint.

| | Arthritis induction | | Daily |
|---|---|---|---|
| | 25 µl Treatment | 200 µg Saline | 0.5 ml M. tb. Drugs |
| Non-arthritic saline + vehicle | L & R | — | Orally |
| Arthritis + vehicle | R | L | Orally |
| Piroxicam 3 mg/kg | R | L | Orally |
| MED 15 25 mg/kg | R | L | Orally |
| MED 15 50 mg/kg | R | L | Orally |
| MED 15 100 mg/kg | R | L | Orally |

Induction of Arthritis

Under halothane anaesthesia, rats received 200 µg of heat-killed finely ground *Mycobactyerium tubercolosis* in 25 µl (80 mg/10 ml sterile saline) injected intra-articulary into the left stifle joint. The contralateral joint received 25 µl 0.9% sterile saline. Control animals received 25 µl of 0.9% sterile saline in both knees. SGE 50 µl microsyringes with a volume lock calibrated at 25 µl were used with 30 G stainless steel needles. Solutions were prepared sterile, and aseptic technique was used throughout, with sterilisation of syringes between groups.

Joint inflammation

The rats were killed by carbon dioxide suffocation. The body weight was noted and the skin overlying the stifle joints was divided and the joint diameters assessed in mm using Mitutoyo vernier callipers (530-312, 0.02 mm).

Patellar bone erosion

The patellae were dissected, weighed (Sartorius, 0.10 mg) and then immersed in 1 ml digestion buffer (see below) to remove soft tissue.

Digestive buffer was prepared fresh to the following formula; disodium hydrogen orthophosphate 20 mM, EDTA 1 mM and diothiothreitol at 2 mM. Papain (EC 3.4.22.2) was added at a concentration of 6 U/ml. Each patella was digested in 1 ml of digestive buffer at 56° C. for 4 hours. The residual paterllar bones were dried (100° C. 24 hours) and weighed (Sartorius 0.01 mg).

Calculations and statistical analysis

Results are presented as follows: left and right parameter alone, the difference between arthritic and contralateral control joint (left-right); and % difference between arthritic and control joints ([left-right]/right]×100).

Units

Joint diameter mm

Patellar bone mass mg

Calculations were carried out using the spreadsheet program Lotus 123. Statistical comparisons were made between the absolute differences using INSTAT Mann Whitney unpaired two-tailed statistical test.

TABLE 9

The effects of daily oral dosing of piroxicam or MED 15 in rat knee joint diameters.

| Treatment | n | Joint diameter (mm) Left | Joint diameter (mm) Right | Swelling Diameter difference (L-R) | % Change |
|---|---|---|---|---|---|
| Non-arthritic vehicle controls | 10 | 8.53 ± 0.08 | 8.63 ± 0.08 | −0.10 ± 0.04 | −1.17 ± 0.51 |
| Arthritic vehicle controls | 10 | 12.22 ± 0.18 | 8.69 ± 0.11 | 3.53 ± 0.15 | 40.66 ± 1.78 |
| Piroxicam 3 mg/kg | 10 | 10.41 ± 0.09 | 8.74 ± 0.05 | 1.67 ± 0.10 | 19.15 ± 1.17 |
| MED 15 25 mg/kg | 10 | 11.57 ± 0.20 | 9.35 ± 0.21 | 2.22 ± 0.14 | 24.04 ± 1.78 |
| MED 15 50 mg/kg | 10 | 10.95 ± 0.14 | 8.88 ± 0.15 | 2.06 ± 0.16 | 23.36 ± 1.98 |
| MED 15 100 mg/kg | 9 | 10.26 ± 0.10 | 8.88 ± 0.15 | 1.38 ± 0.14 | 15.71 ± 1.73 |

Patellar Bone Mass

Table 10 shows the effects of drug treatments on patellar bone mass. There was a large reduction in bone mass in the arthritic (p<0.0001) groups compared to the non-arthritic group reflecting erosion. Although there was no statistically significant difference in the loss of bone mass of the arthritic groups the piroxicam treated group showed the greatest protection against bone loss. MED 15 displayed a dose dependent protective effect which was not significantly different to piroxicam at a dose of 100 mg/kg.

TABLE 10

The effects of daily oral dosing of piroxicam or MED 15 on rat patellar bone mass.

| Treatment | n | Bone mass (mg) Left | Bone mass (mg) Right | Bone loss Left-Right (mg) | % Change |
|---|---|---|---|---|---|
| Non-arthritic vehicle controls | 10 | 3.59 ± 0.16 | 3.73 ± 0.11 | −0.09 ± 0.13 | −3.39 ± 2.90 |
| Arthritic vehicle controls | 10 | 2.03 ± 0.31 | 3.96 ± 0.15 | −1.93 ± 0.34 | −48.06 ± 7.97 |
| Piroxicam 3 mg/kg | 10 | 3.07 ± 0.13 | 4.21 ± 0.09 | −1.31 ± 0.11 | −27.74 ± 2.26 |
| MED 15 25 mg/kg | 10 | 2.33 ± | 4.27 ± | −1.94 ± | 45.45 ± |
| MED 15 50 mg/kg | 10 | 2.49 ± 0.14 | 4.18 ± 0.10 | −1.69 ± 0.12 | 40.55 ± 2.82 |
| MED 15 100 mg/kg | 9 | 2.97 ± 0.12 | 4.34 ± 0.08 | −1.38 ± 0.08 | 31.85 ± 1.93 |

Toxicological Profile

From a toxicological viewpoint the drug offers an excellent torability profile. In fact, the drug safety trials demonstrated absence of effects on blood pressure and on the cardiovascular system (b.r. No. 4).

Acute toxicity studies (b.r. No. 5), indicated excellent drug tolerability. Studies carried out by the Hazleton laboratories (b.r. No. 6 and 7) in particular, demonstrated absence of gastric damage following chronic oral administration for 52 weeks in the rat and in the Cynomolgous monkey.

The fertility, embriotoxicity and teratogenicity studies in the rat and in the rabbit (b.r. No. 8, 9 and 10) demonstrated the safety product.

In the same way the Ames test (b.r. No. 11), forward mutation in Saccharomycetes pombe P1 (b.r. No. 12), mitotic conversion in Saccharomycetes D4 (b.r. No. 13), chromosomic aberrations in human lymphocites cultivated in vitro (b.r. No. 14), micronucleus test in rat bone marrow (b.r. No. 15) all demonstrated absence of amtolmetin guacyl-related damage.

Carcinogenesis studies in the rat administered by gavage with amtolmetin guacyl for a period covering the animal's life-span (b.r. No. 16) demonstrated the innocuity of the product.

3) Mechanism of action

Interest in the amtolmetin guacyl molecule arose following a thorough analysis of the results of 31 comparative and 6 non-comparative clinical trials involving 1596 patients. All of the studies revealed an extremely low incidence of adverse events involving the stomach (5% circa) which compared the product very favourably with the other NSAIDs, in which the incidence was in the region of 30% or more (as in the case of indomethacin) with frequent interruptions of treatment. This 5% was considered by us to be practically hull in consideration of the fact that all of the patients reporting side effects frequently had a past history of concomitant disease and previous medical treatment; also, it cannot be excluded that antihistamine drugs were taken during the course of the experimentation which are known to interfere with the mechanisms of gastric protection of amtolmetin guacyl. Furthermore the physician, being aware of administering an NSAID, was expecting adverse events and could not be expected to be an impartial observer. The few cases of gastro-intestinal phenomena reported with amtolmetin guacyl were transitory and in no event accompanied by the presence of occult blood in the stools. Moreover, even in the presence of a reported side-effect it was almost never necessary to suspend treatment (0.4% of suspensions).

Figure 5:
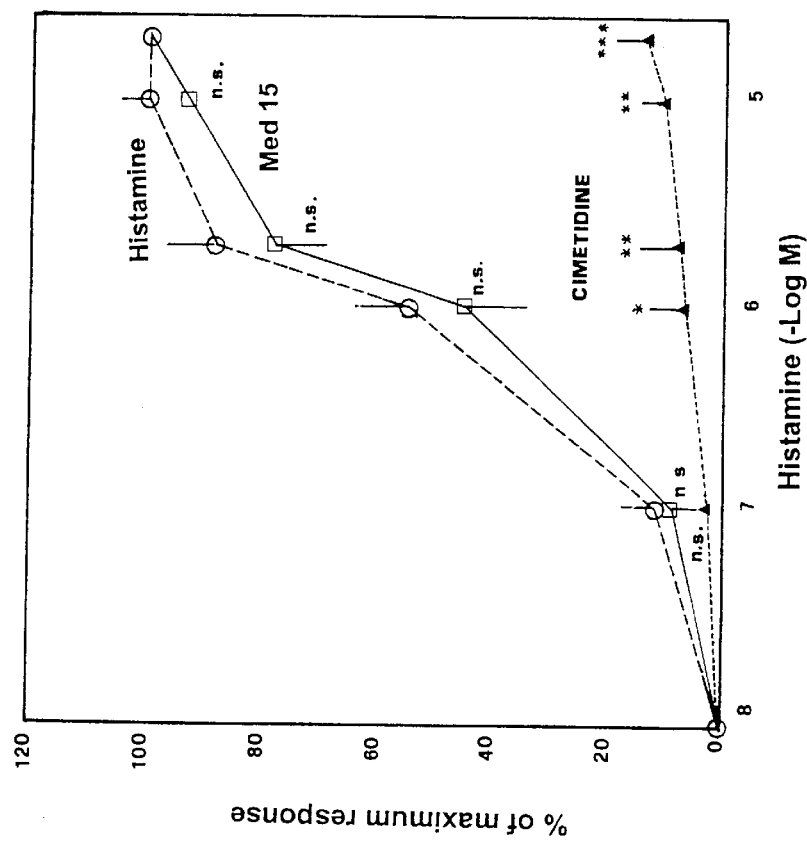
FIG. 5 shows the effect of amtolmetin guacyl on the $H_2$-receptors of the guinea pig isolated atrium; the stimulation was produced by histamine.

On the basis of the above series of observations, we decided to study the pharmacological behaviour of a number of widely used NSAIDs (including amtolmetin guacyl)

towards the gastric mucosa in the rat, as previously described. Having univocally established the effect of amtolmetin guacyl on the reduction of gastric acid, the question of the mechanism of action of this effect arose. The first hypothesis was that we were deling with an anti-$H_2$ drug, given the fact that its potency could be compared with that of cimetidine. However, when using an organ in which only $H_2$ receptors were present (guinea-pig atrium) the drug did not interfere with the $H_2$ receptors (FIG. 5).

On the other hand, we had previously noted differences between potentiometric determination of H+ and NaOH titration of the gastric effluate, in agreement with the substantial literature available on the subject, This fact was clearly in favour of a strong presence of bicarbonates (b.r. No. 27, 28).

Figure 6:
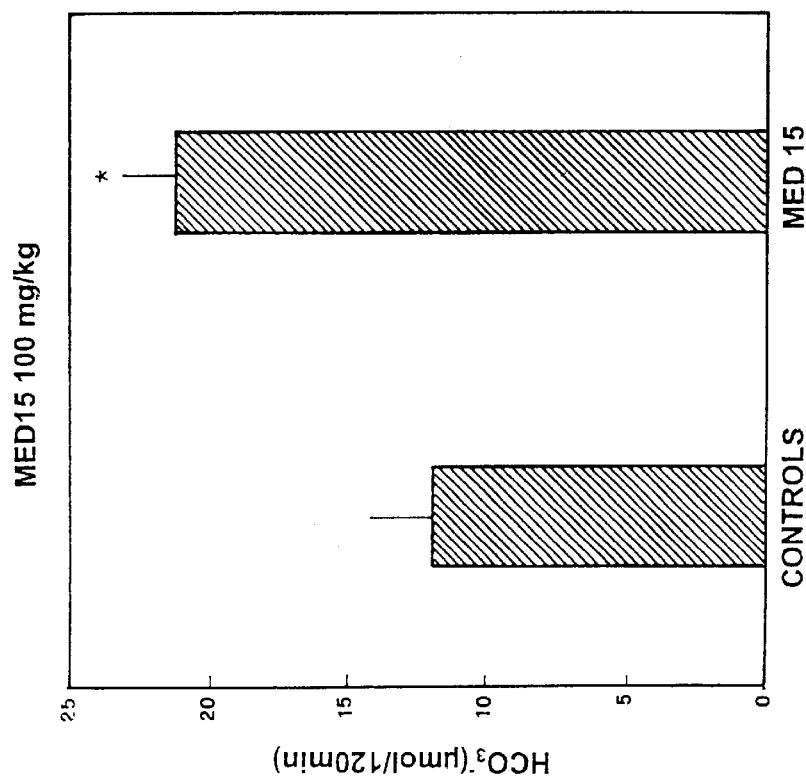
FIG. 6 shows the effect of amtolmetin guacyl on gastric bicarbonate secretion in the rat, using histamine as a stimulating agent.

Experiments on bicarbonate secretion (under the same conditions as these of the acid secretion studies) following stimulation with histamine and treatment with amtolmeting guacyl, demonstrated an increase in bicarbonate production of 67% (FIG. 6).

Figure 7:
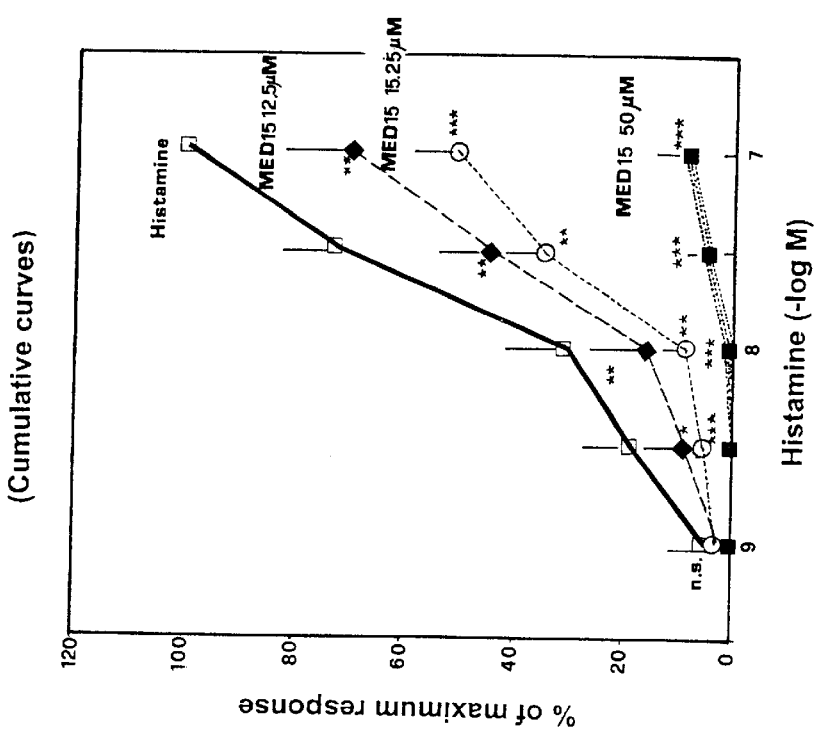
FIGS. 7 and 8 show the antispasmodic effect of amtolmetin guacyl on guinea pig isolated ileum, using as a stimulating agent histamine and acetylcholine (cumulative curves)
Figure 8:
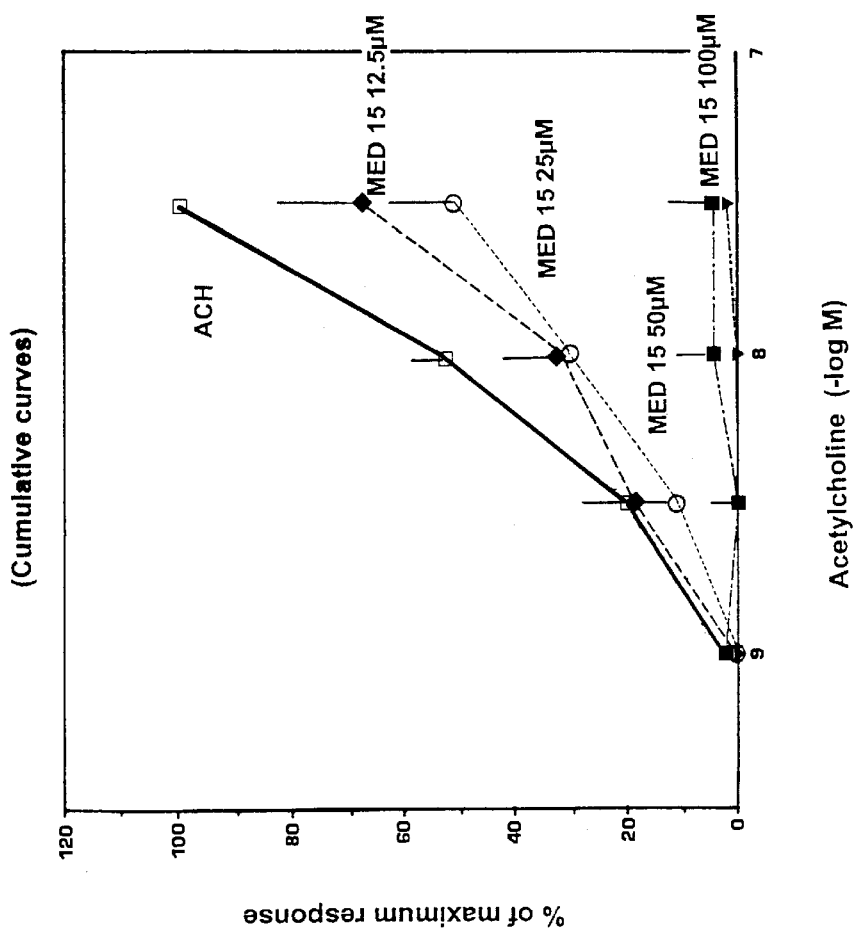
Figure 9:
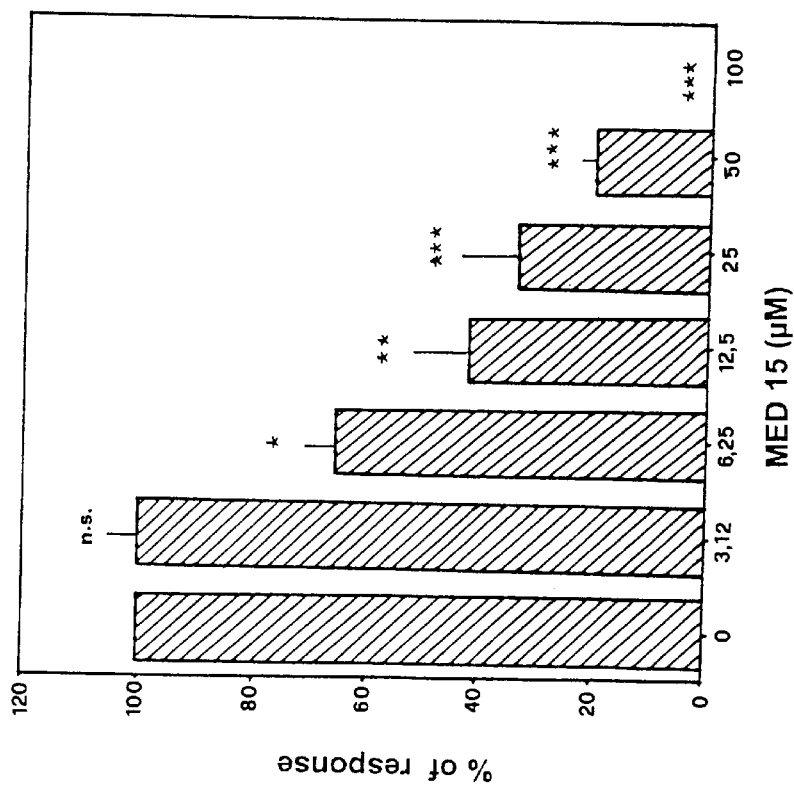
FIG. 9 shows the antispasmodic effect of amtolmetin guacyl on guinea pig isolated ileum, using as a stimulating agent serotonin.

In parallel we also studied the possible effect on intestinal motility in the guinea-pig isolated ileum (b.r. No. 29) using various agonists (FIG. 7, 8 and 9)

Figure 10:
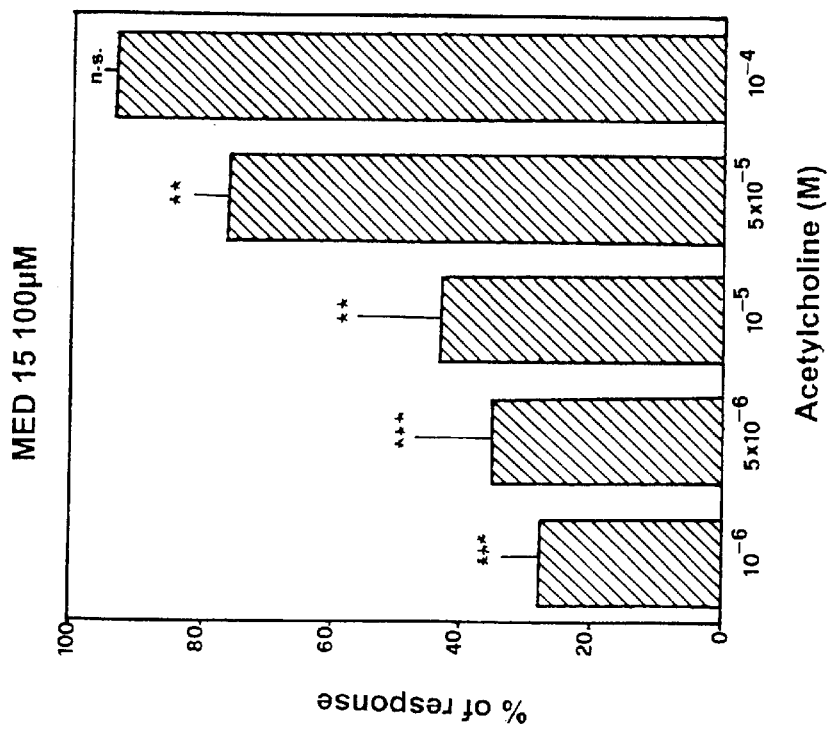
FIGS. 10 and 11 show the effect of amtolmetin guacyl on gastric motility in the rat, using respectively increasing doses of acetylcholine and serotonin, while FIG. 12 the dose-effect relationship of amtolmetin guacyl on gastric motility in the rat.
Figure 11:
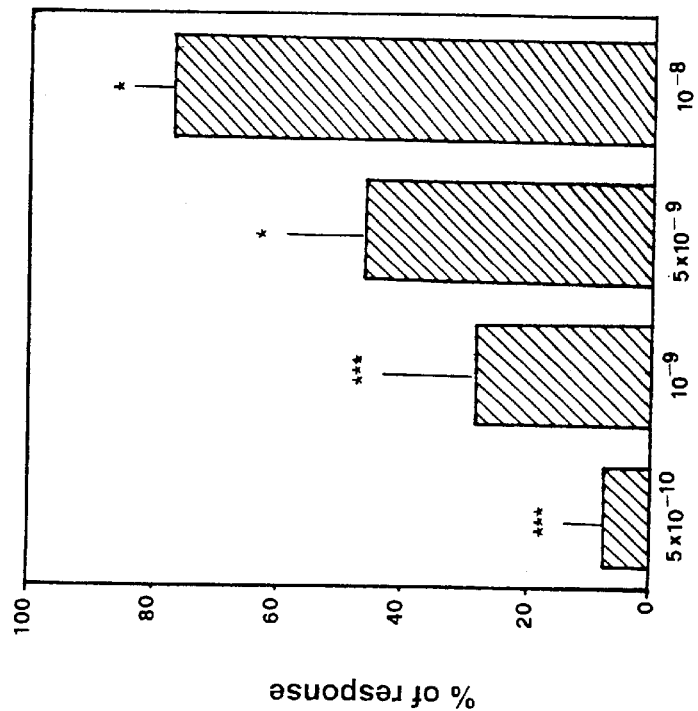
Figure 12:
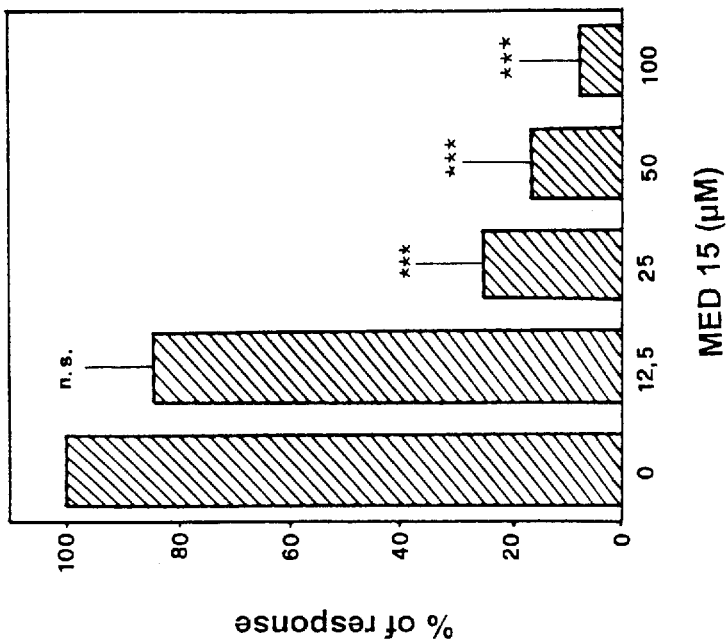

Having established the amtolmeting guacyl-related decrease in motility using all of the traditional agonists, we proceeded to verify whether this same effect was present at gastric level. Using acetilcholine and serotonin as agonists in the rat isolated stomach strips model (b.r. No. 30), we obtained clear evidence of down-regulation of motility also in this organ (FIG. 10, 11 and 12).

Figure 13:
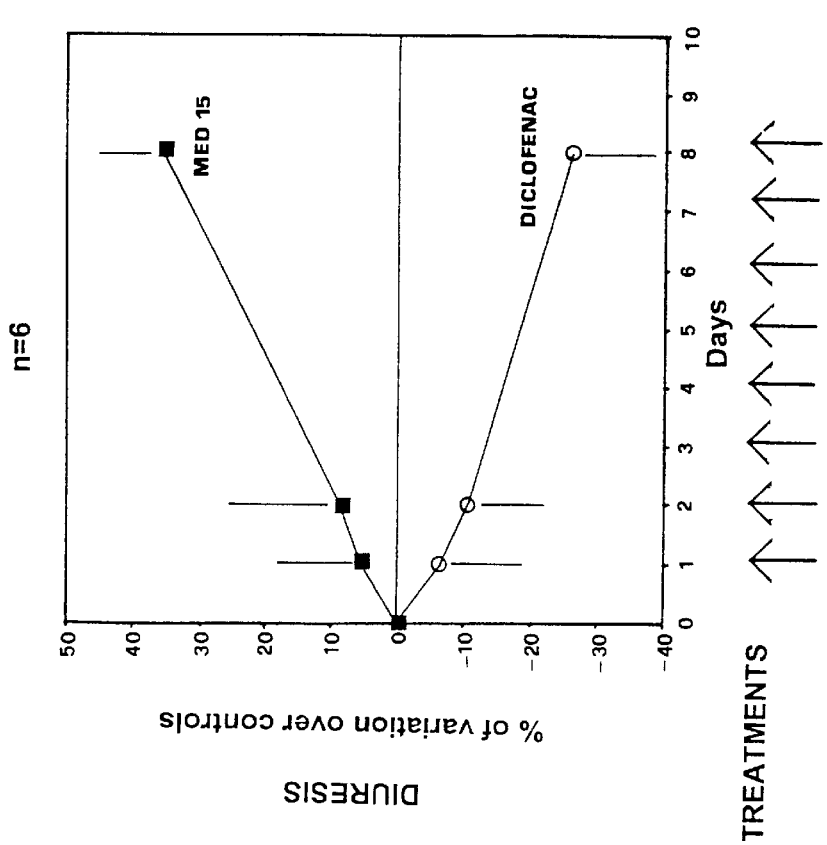
FIG. 13 shows the effect of amtolmetin guacyl and of diclofenac on rat diuresis.

In the course of various studies conducted on animals to show the lack of renal impairment, a test was carried out to compare the diuresis in normally hydrated rats treated orally for 8 consecutive days with amtolmeting guacyl and diclofenac, which is also a NSAID. From the results, which are shown in FIG. 13, it is possible to observe a definite increase in diuresis in the animals which were treated with amtolmeting guacyl and a likewise clear decrease in the animals treated with diclofenac. It is to be stressed that the behaviour of diclofenac is completely in line with the behaviour of a NSAID as known in the art, that is to say to markedly reduce the diuresis, while that of amtolmeting guacyl is completely unforeseeable.

The results obtained led to the identification of a mechanism of action which would simultaneously account for:

1)—decrease of acidity
2)—increase of bicarbonates
3)—increase of gastric blood flow
4)—increase of diuresis
5)—decrease of motility.

At this stage CGRP (calcitonin gene related peptide) was considered a good candidate to match with all of the parameters to be considered. CGRP is a 37 aminoacid polipeptide which depresses gastric acidity (b.r. No.31, 32).

Figure 14:
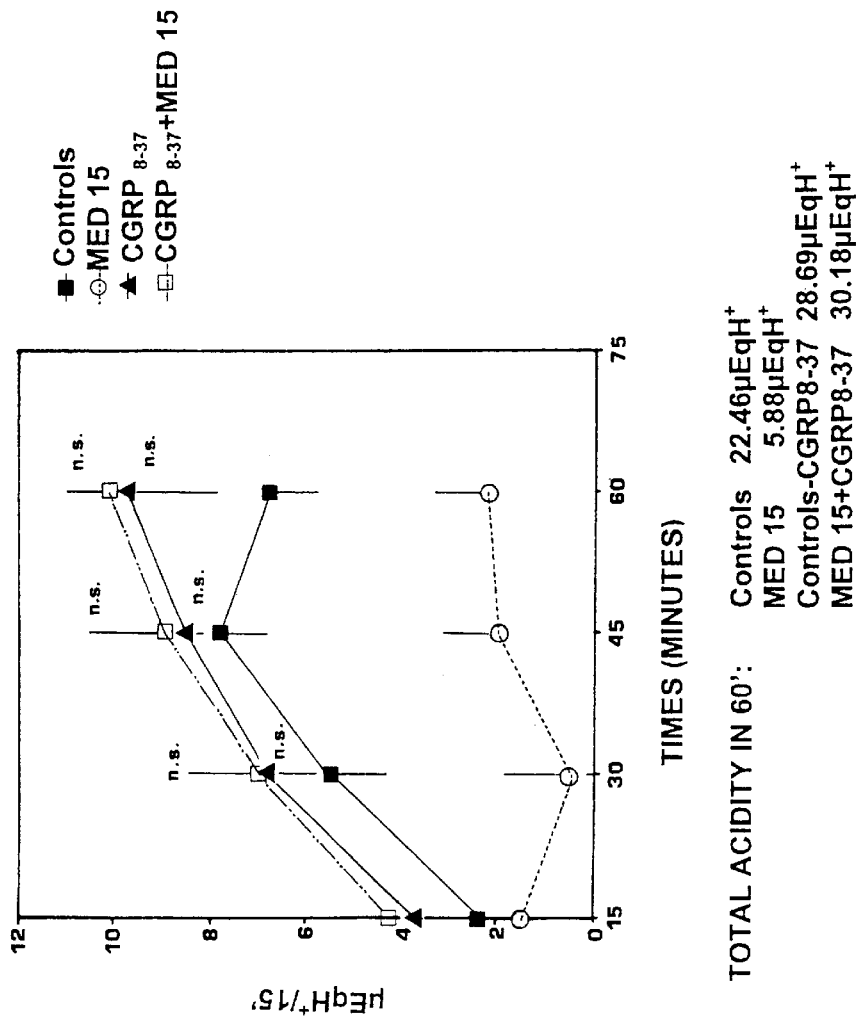
FIG. 14 shows the effect of amtolmetin guacyl on peptone-stimulated gastric acid secretion in the rat following treatment with $CGRP_{8-37}$.

Experiments carried out using a specific antagonist of CGRP ($CGRP_{8-37}$) demonstrated that inhibition of this polipeptide leads to blockage of the amtolmetin guacyl related activity on gastric secretion. This demonstrates thet CGRP actually is implicated in the mechanism of action of amtolmetin guacyl (FIG. 14).

These results were confirmed by Huntingdon Life Sciences U.K.

CGRP production itself is known to be stimulated by the vanilloid (or capsaicin) sensitive receptors which simultaneously produce an increase in bicarbonate production (b.r. No. 33). A comparison between the capsaicin structures and amtolmetin guacyl shows that all of these structures contain a vanilloid radical in their molecules (FIG. 15).

Figure 16:
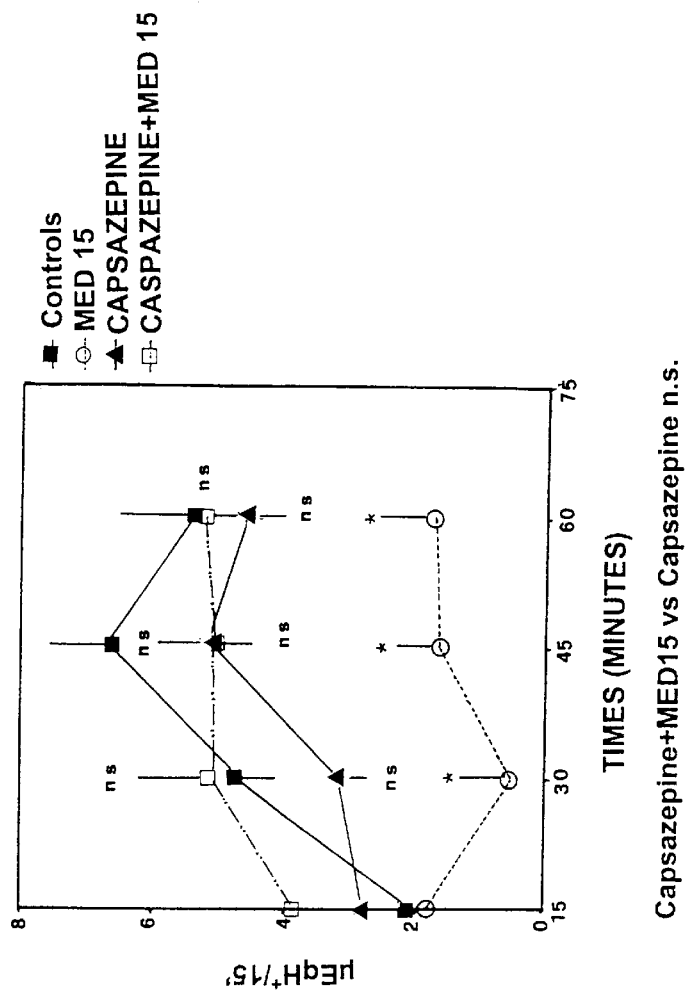
FIG. 16 shows the effects of amtolmetin guacyl on peptone-stimulated gastric acid secretion in the rat following treatment with capsazepine.

The hypothesis of the impact of amtolmetin guacyl on the vanilloid receptors was therefore strengthened and the experimental demonstration was obtained using capsazepine, a specific receptor antagonist of capsaicin (FIG. 16). The introduction of a guaiacol moiety into the amtolmetin guacyl molecule led to the insertion of a vanilloid radical which confers gastroprotective properties to the molecule. Moreover, although capsaicin possesses revulsive and inhibitory properties, both nonivamide and amtolmetin guacyl are inhibited by the capsazepine antagonist, and do not determine any irritative phenomena (b.r. No. 34, 35, 36).

Figure 17:
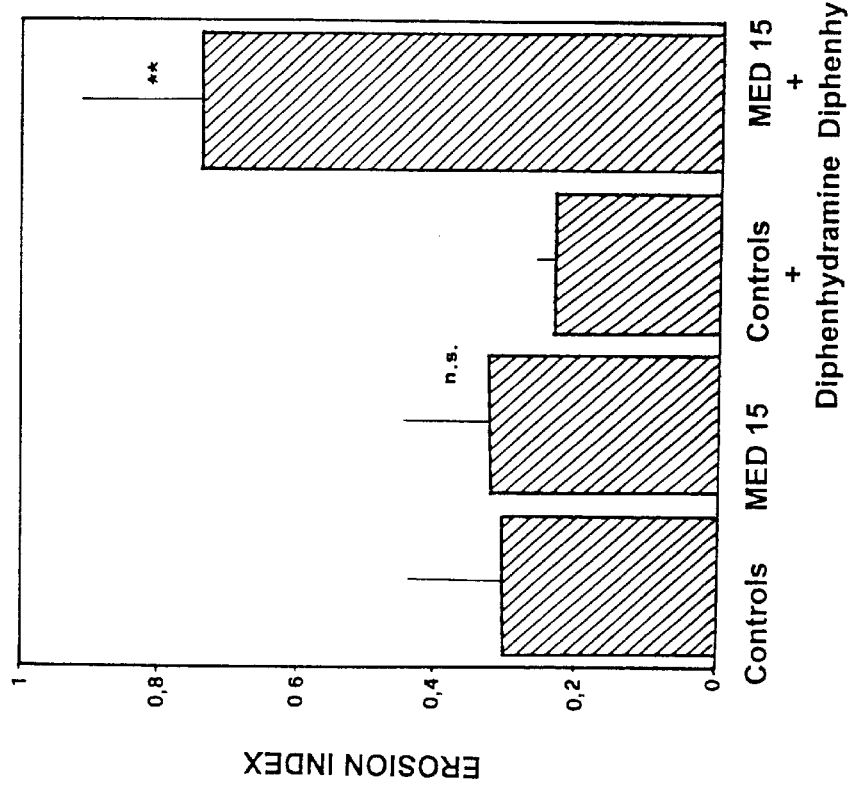
FIG. 17 shows the interference of diphenhydramine on gastroprotective action of amtolmetin guacyl in the rat.
Figure 18:
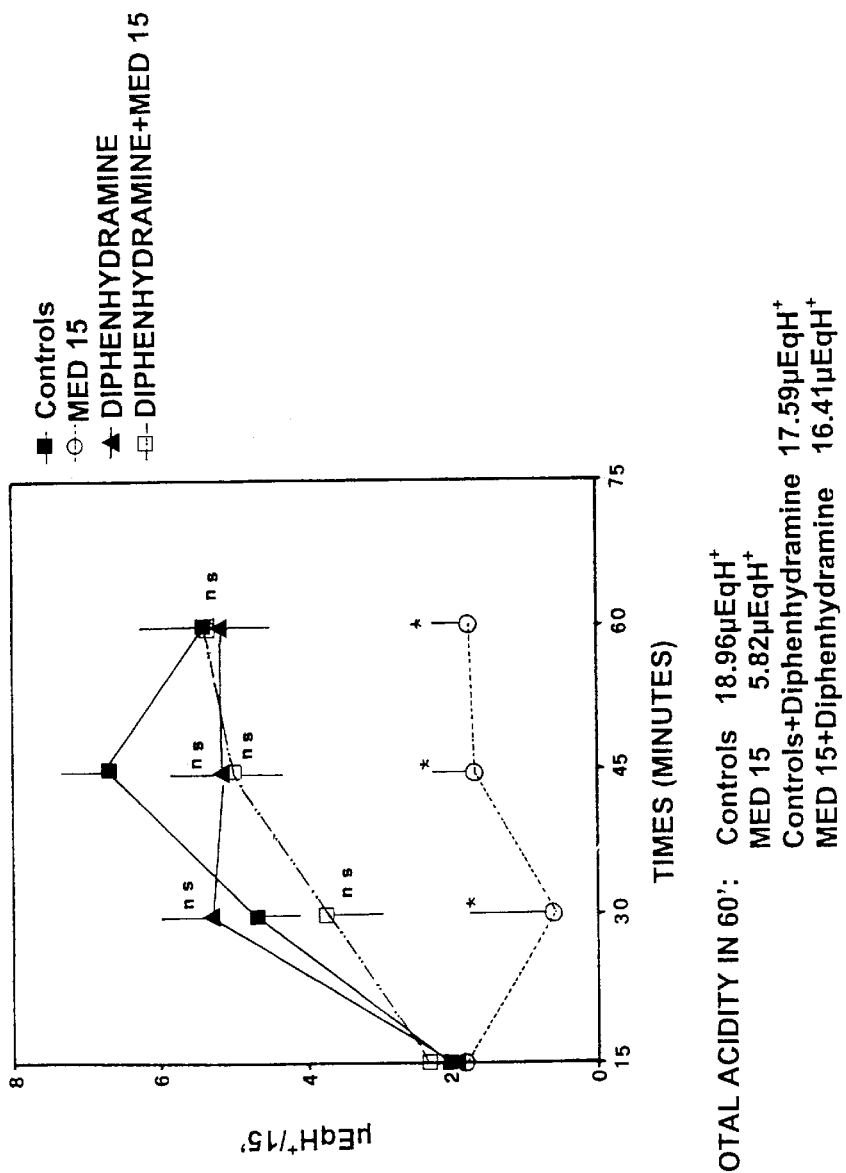
FIG. 18 shows interference of diphenhydramine on the effect of amtolmetin guacyl on peptone-stimulated gastric acid secretion in the rat.

In the in vivo experimentation, evaluated as effect of the product both on gastric mucosal secretion and on the healthy condition of the mucosa itself, it was noted that in the presence of an inhibitor of $H_1$ receptors (therefore a typical antihistamine agent), the gastroprotective effect of amtolmetin guacyl drops out. This is a further demonstration of the impact of amtolmetin guacyl on the vanilloid receptors, due to the well known interference existing between these receptors and drugs such as diphenidramine (b.r. No. 37) and pyrilamine (b.r. No.38). All of this constitutes a precise forewarning of the association of amtolmetin guacyl with $H_1$ receptor inhibiting substances on pain of loss of the gastroprotective properties of the former (FIG. 17 and 18).

The presence of the vanilloid radical, essential to the expression of the gastroprotective mechanism, is guaranteed by the prolonged persistence of high amounts of intact amtolmetin guacyl molecule in the gastric and intestinal walls (at least 2 hours after oral administration in the rat).

CGRP down-regulates acid secretion and also produces intense vasodilation of gastric mucosa and of the kidney, where it produces an increase in glomerular infiltration rate (which justifies the diuretic effect of amtolmetin guacyl) (b.r. No. 39). Also, the decrease in amtolmetin guacyl-determined motility which we observed may be attributed to increased CGRP, a notorious inhibitor of gastrointestinal motility (b.r. No. 40).

Recent studies indicate that the vasodilatatory and cytoprotective effects of CGRP at the gastric level implicate, at least in part, NO-dependent mechanisms (b.r. No. 41). Implication of nitric oxide in the smooth muscle relaxation exercised by CGRP has also been demonstrated (b.r. No. 42).

Glycine is released during the metabolic processes of amtolmetin guacyl. Since glycine determines an increase in glomerular filtrate and this effect is inhibited by an antagonist of NO synthesis, it is legitimate to consider NO as the mediator of the action exercised on this mechanism by glycine. Hence, since NO is implicated in the mechanism of action of CGRP and of glycine, and the latter aminoacid is one of the amtolmetin guacyl metabolites, we may deduce that glycine also contributes to the positive renal effects exercised by the product.

From the results summarized above amtolmetin guacyl emerges as an NSAID with a completely new profile necessitating specific indications in user in particular, being an anti-secretory drug and inhibitor of gastric motility, it has to be administered on an empty stomach so as not to interfere with normal digestive processes. It has to be stressed that this is the first case in which a NSAID is administered on empty stomach, while all other NSAIDs administered invariably after meals. Moreover, for what explained above, amtolmetin guacyl in order to have its gastro- and renal-protective effect has to be administered without concomitant assumption of $H_1$-receptor inhibiting drugs.

In conclusion, the data presented indicate that amtolmetin guacyl is an anti-inflammatory drug with outstanding characteristics, which make its use possible in patients in whom the administration of NSAIDs is usually contraindicated.

4) Clinics

Once the mechanism of action of MED 15 was found and its pharmacology defined we proceeded to establish the efficacy and tolerability in man.

The pharmacodynamic profile of amtolmetin guacyl must necessarily depart from its antiphlogistic and antalgic properties, the two aspects of most interest to both the patient and the physician.

To do this we must analyze the different efficacy of amtolmetin guacyl compared with some of the most widely used NSAIDs in the treatment of the four following conditions:

1)—rheumatoid arthritis
2)—osteoarthritis
3)—extra-articular rheumatism
4)—post-operatory pain.

Following are summarized the results obtained on a total of 1596 patients in 37 clinical trials Rheumatoid Arthritis Amtolmetin guacyl was compared with ibuprofen, indomethacin, piroxicam and tolmetin.

As reported in Table 11, when administered to 150 patients with rheumatoid arthritis in the active phase Amtolmetin guacyl demonstrated significantly more rapid and marked anti-inflammatory activity compared to the reference NSAIDs.

The anti-inflammatory activity of Amtolmetin-guacyl in rheumatoid arthritis would make it the product of choice in the treatment of this disease.

TABLE 11

| Indication: rheumatoid arthritis | |
| --- | --- |
| Patients: | 150 |
| Days of treatment: | 30 |
| Reference NSAIDs: | Ibuprofen |
| | Indomethacin |
| | Piroxicam |
| | Tolmetin |
| Evaluation of antiphlogistic activity: | Amtolmetin guacyl demonstrated statistical significant activity more rapid and more marked when compared to the reference NSAIDs in rheumatoid arthritis. |

Osteoarthritis

In this degenerative disease amtolmetin guacyl was compared with diclofenac, diflunisal, flurbiprofen, ibuprofen, ketoprofen, naproxen and tolmetin. Amtolmetin guacyl demonstrated statistically significant more rapid and more marked activity, as reported in Table 12.

TABLE 12

| Indication: osteoarthritis | |
| --- | --- |
| Patients: | 550 |
| Days of treatment: | mean 80 |
| Reference NSAIDs: | Diclofenac |
| | Diflunisal |
| | Flurbiprofen |

TABLE 12-continued

| Indication: osteoarthritis | |
| --- | --- |
| | Ibuprofen |
| | Ketoprofen |
| | Naproxen |
| | Tolmetin |
| Evaluation of antiphlogistic activity: | Amtolmetin guacyl was more rapid and more active in a statistically significant manner in osteoarthritis compared to the reference NSAIDs. |

The anti-inflammatory activity of amtolmetin guacyl in osteoarthritis would make it the product of choice in the treatment of this disease.

Extra-articular rheumatism

In extra-articular rheumatism amtolmetin guacyl was compared with diclofenac, naproxen and piperazine propionate. The results are shown in Table 13.

TABLE 13

| Indication: extra-articular rheumatism | |
| --- | --- |
| Patients: | 90 |
| Days of treatment: | 14 |
| Reference NSAIDs: | Diclofenac |
| | Naproxen |
| | Piperazine propionate |
| Evaluation of antiphlogistic activity: | In this indication no significant differences were noted between amtolmetin guacyl and the reference compounds. |

Post-operative Pain

As reported in Table 14, the analgesic properties of amtolmetin guacyl were tested in postoperative pain with good results.

The same can be said in the treatment of post-traumatic arthralgia.

TABLE 14

| | Indication: a) post-operative pain b) post-traumatic arthralgia | | | | |
| --- | --- | --- | --- | --- | --- |
| N. patients | Dose | Latency (mins.) | Max. time | effect (mins.) | Duration (mins.) |
| a) Amtolmetin guacyl | 100 | 1200 mg | 30 | 180 | 360 |
| b) Amtolmetin guacyl | 15 | 600 mg × 2-daily* | 20 | 60 | 360 |
| c) Diclofenac | 15 | 50 mg × 2-daily* | 20 | 60 | 180 |

*at 12-hour intervals

The data obtained indicate that the antalgic effect is statistically significant in post-operative pain and this effect is already evaluable at 30' following administration. The peak effect is obtained only after 2 hours, and it is maintained for 6 hours.

When compared with diclofenac in post-traumatic arthralgia Amtolmetin guacyl showed the same latency time (20 minutes), the same time to reach peak effect (1 hour), but a longer duration of effect (6 hours as opposed to 3 hours).

CONCLUSIONS

Clinical studies demonstrate that amtolmetin guacyl has very marked anti-inflammatory activity, primary in the treatment of rheumatoid arthritis, osteoarthritis and post-operative pain. There were no differences compared to the other NSAIDs in the treatment of extra-articular rheumatism. The results are summarised in Table 15.

The singularity of the compound lies in the long duration of the peak effect (6 hours), unlike all of the other NSAIDs.

TABLE 15

Antiphlogistic activity

| Rheumatoid arthritis | ++++ |
| Osteoarthritis | ++++ |
| Post-operative pain | ++++ |
| Extra-articular rheumatism | +++ |

Antiphlogistic activity evaluation: excellent ++++ good +++, poor ++

II Parameter: Tolerability

Drug tolerability is important for the correct calculation of the risk/benefit ratio. Of relevance for NSAIDs is the recognition of gastric (A) and renal (B) side-effects.

A) NSAIDs and gastric damage

The incidence of the undesirable side effects of NSAIDs on the gastric mucosa varies depending on the drug structure and its pharmaceutical form. The buffered effervescent formulations, for example, avoid the gastric mucosa/compound primary damage but not damage the mucosa after re-cycling.

With the NSAIDs known to date the incidence of side effects involving the gastric mucosa is about 20–30%, the elderly, in whom the adaptive processes are often slowed down or compromised, being the most affected.

NSAID-related gastric damage is due to the inhibition of gastric prostaglandins which results in a NSAID-related hydrochloric acid hypersecretion; in fact NSAIDs by inhibiting all prostaglandin synthesis (and this is inherent to their anti-inflammatory activity), also protective prostaglandins of the gastric mucosa.

Amtolmetin guacyl and gastric protection Amtolmetin guacyl shows good anti-inflammatory activity in man and the pharmacological studies conducted in rats showed that this effect is due to inhibition of both COXI (cyclooxygenase 1) and COX2 (cyclooxygenase 2).

Amtolmetin guacyl therefore also inhibits the COX1 known to induce the synthesis of those prostaglandins which protect the gastric mucosa and the renal flow as well as the synthesis of $TXA_2$ (thromboxane $A_2$), a potent platelet aggregating agent. For all of these reasons the drug was expected to induce gastric damage and inhibit platelet aggregation.

Amtolmetin guacyl does indeed demonstrate significant platelet antiaggregating properties, but it has also demonstrated in clinics (with before/after endoscopies) not to induce gastric lesions, especially when administered on an empty stomach.

The mechanism of action of amtolmetin guacyl is linked to stimulation of both vanilloid receptors and CGRP (calcitonin gene-related peptide) receptors, as demonstrated using specific inhibitors. Moreover, the structure of MED 15 contains a vanilloid moiety; this appears to be the reason for its specific stimulating effect. The various chemical structures are reported in FIG. 15 for comparison.

Amtolmetin guacyl per se fails to modify basal acid secretion; its gastroprotective effect arises only when H+ production exceeds a certain limit.

B) Renal tolerability.

Inhibition of prostaglandin synthesis is known to reflect negatively on renal function since prostaglandins are delegated to the modulation of renal blood flow and they are physiologically released to counteract the renovasoconstriction produced by angiotensin II.

CGRP overflow from the stomach into the bloodstream produces visible effects in patients (red flushed appearance) and effects on the kidney (increase in diuresis), counteracting the effects of prostaglandin inhibition.

To shed some light on the possible exploitation of this unexpected effect on the kidney we listed the classes of patients which show the highest risk of developing renal failures when treated with NSAIDs.

TABLE 16

Patient groups at highest risk of developing NSAID-induced renal failure

| Certain: | congestive heart failure |
| | hepatic insufficiencies with ascites |
| | nephrosis |
| | disorders involving decrease of blood volume (ex. dehydration) |
| | chronic glomerulonephritis |
| | chronic renal failure |
| | systemic lupos erythematosus |
| | multiple myeloma |
| Possible: | the elderly (especially diabetics and hypertensives) |
| | atherosclerotic-related cardiovascular disease |
| | gouty arthritis (precipitated by diuretics in the elderly) |
| | patients submitted to general anaesthesia |
| | patients with sepsis, endotoxemia and serious infections |
| | concomitant diuretic treatment |
| | patients on low-salt diets |
| | chronic pyelonephritis |

Amtolmetin guacyl and renal function

Despite the fact that amtolmetin guacyl is a NSAID, it has been surprisingly found that it antagonizes the renal vasoconstriction provoked by the inhibition of prostaglandin synthesis.

As proof of the above, studies carried out in rats demonstrated that a single dose of Amtolmetin guacyl increased diuresis in these animals by an average of 10%, whilst diclofenac decreased it by an average of 10%.

Repeated doses (one per day) for 8 days increased diuresis in the treated rats by 35% (see FIG. 13).

Tolerability: conclusions The tolerability of amtolmetin guacyl is very good and no significant variations of the routine biological parameters were observed during or after treatment.

The organs most open to damage by the NSAIDs, the gastrointestinal system and the kidneys, benefit from the protective activity of Amtolmetin guacyl, without detriment to the therapeutic activity of the drug.

At present in clinics NSAID-related side-effects are minimized by the simultaneous delivery of $H_2$-receptor antagonists or protonic pump inhibitors or gastroprotective prostaglandins. All these treatments have their own side-effects. In our case this protective effect is obtained with a single drug, improving therapy acceptability on the part of the patient, especially in the long-term treatments.

Confirmation of the above described advantages is the very low incidence of treatment suspension for adverse events found in clinics (Table 17), which is not the case for most of NSAIDs known in the art (Table 18).

Table 17 reports the results of amtolmetin guacyl in a cohort of 949 patients.

TABLE 17

Suspensions of treatment for adverse events with amtolmetin guacyl

| Days of treatment | N. patients | Treatment | suspended % |
|---|---|---|---|
| 10 | 190 | 3 | 1,6 |
| 21 | 70 | 0 | |
| 30 | 140 | 1 | 0,7 |
| 60 | 225 | 0 | |
| 90 | 225 | 0 | |
| 120 | 25 | 0 | |
| 150 | 49 | 0 | |
| 180 | 25 | 0 | |
| Total | 949 | 4 | 0,4 |

TABLE 18

Incidence of treatment suspension for adverse events: meloxicam and diclofenac

| | Meloxicam | Diclofenac 100 mg |
|---|---|---|
| Days of treatment | 180 | 180 |
| N. patients | 336 | 336 |
| Suspensions of treatment | 42 | 63 |
| % of total | 12,4 | 18,7 |

As can be seen from this table, the differences of tolerability between Amtolmetin guacyl, meloxicam and diclofenac appear wide; it must be taken into consideration that the 6-month (a total of 60.480 days) duration of the meloxicam and diclofenac studies well compares with the duration of the Amtolmetin guacyl studies (a total of 56.170 days)

In any case all reports of gastric discomfort (4%) were of a minor nature resolved spontaneously during the course of the treatment. These minor events may be explained by the possibility that the drug was taken meals or in concomitance with antihistamine (anti-$H_1$) agents, which inhibit the gastroprotective effect of amtolmetin guacyl whilst maintaining its antiinflammatory effect. Consequently amtolmetin guacyl, to show its activity, has to be administered on empty stomach and without a concomitant administration of $H_1$-receptor inhibiting drug.

In summary, due to its antiinflammatory properties and protective effect on the stomach and kidney, the following patient categories are specifically good responders to MED 15 treatment:

subjects with a need for a long term treatment with a NSAID, subjects with specific gastric and/or renal intolerance to NSAID's, subjects with preexisting gastritis and/or gastric and/or gastroduodenal lesions, subjects with NSAID-related renal impairment due to vasoconstriction, subjects with reduced renal function or in damage thereof.

Inhibitory effect of MED 15 on platelet aggregation.

At the present state of the art, patients in need of an antiaggregating treatment in order to avoid platelet sticking are normally treated with acetyl salicylic acid or, as an alternative, with a NSAID. The administration takes normally place over a long term; in some cases (for instance patients who suffered from an infarct) the administration of the drug has to be prolonged for all the life. One of the main problems in the administration of acetyl salycilic acid and, of NSAIDs in general, is That patients have or may develop an intolerance to this kind of drugs, one of the reasons is that this drugs are known to be gastrolesive which fact renders it difficult, if at all possible, a long-term treatment.

MED15 has demonstrated inhibitory effects on platelet aggregation in vitro in the rat, and to induce inhibition of $TXB_2$ plasma levels comparable to the effect of ASA (acetyl salicylic acid). The following pharmacological tests have been carried out in order to show the inhibitory effects on platelet aggregation of MED 15.

Chemicals and Animals used.

1. Chemicals.

Collagen, arachidonic acid sodic salt, acetyl salicylic acid and carboxymethylcellulose (CMC)[Sigma Chimica, Milano]; amtolmetin guacyl [Alpha Chemicals Italiana, Bergamo]; sodium citrate [Merck, Germania].

2. Animals.

New Zealand Male Rabbits 200–300 g [Stefano Morini, S. Paolo D'Enza, RE Italia], quarantined for 5 days before the beginning of the experiments (anti-aggregating effect on platelets).

Male Wistar Rats, 250±20 g [IFFA CREDO Italia] randomized and divided in groups of 5 animals each were starved for 16 hours before the treatment (determination of the thromboxanemie) . The animals received a standard commercial diet with free access to water. For the whole duration of the experiments they were maintained to the following condition: temperature 22±2° C., relative humidity 55±10%, light/dark cycle 12 h.

3. Determination of platelet aggregation on PRP (plasma rich in platelets) of rabbit.

The blood was taken from the rabbits through the heart using sodium citrate as an anti-coagulant agent at a final concentration of 0,38% and centrifuged for 16 minutes to 150 g to obtain a PRP. The PRP obtained was used at a concentration of $3 \times 10^8$ platelet/ml. MED 15 and the other products were incubated with the PRP for 3 minutes at 37° C. before adding the aggregating agent. The platelet aggregation induced by arachidonic acid, sodium salt [TAC (threshold aggregation concentration) : 140 $\mu$m] and collagen (TAC: 28 $\mu$g/ml) has been carried out using an aggregometer (Chronolog mod. 500) according to the method of Born (Borg G. V. R. Nature 1962; 194:927–929) and it has been expressed as percentage of inhibition with respect to the average response of the agonist.

4. Determination of thromboxanemie in rat.

MED 15 and ASA (acetyl salicylic acid) suspended in carboxymethylcellulose (CMC) 1%, were administered orally to the animals at the dosage of 100 mg/kg (1,5 ml/rat) and the controls received only CMC. The blood samples obtained from the heart 3 hours after the treatment, were incubated at 37° C. for 60 minutes and centrifuged for 10 minutes at 3600 rpm. In the so obtained serum the content of thromboxane was determined using a RIA kit [Amersham TRK780]. The results obtained may be evaluated with reference to the following tables and figures.

FIG. 19 shows the inhibition (%) of aggregation of rabbit platelets comparing the effect of MED 15 with that of tolmetin at various dosage using as agonist collagen (FIG. 19a) and arachidonic acid (FIG. 19b, respectively). The following tables 19 and 20 show the anti-aggregating effect of MED 15 in vitro in comparison with ASA (acetyl salicylic acid) using as agonist arachidonic acid (table 19) and collagen (table 20).

TABLE 19

Anti-piastrinic effect in vitro of MED 15 in comparison with ASA
Agonist: Arachidonic acid sodium salt

| Substance | Dose ($\mu$M) | Inhibition % |
|---|---|---|
| MED 15 | 5,0 | 100,0 |
|  | 2,5 | 100,0 |
|  | 1,25 | 100,0 |
|  | 0,5 | 7,7 |
| ASA | 100,0 | 100,0 |
|  | 50,0 | 83,3 ± 16,7 |
|  | 25,0 | 0 |

TABLE 20

Anti-piastrinic effect in vitro of MED 15 in comparison with ASA
Agonist: collagen

| Substance | Dose ($\mu$M) | Inhibition % |
|---|---|---|
| MED 15 | 0,39 | 100,0 |
|  | 0,10 | 34,3 |
|  | 0,05 | 0 |
| ASA | 100,0 | 100,0 |
|  | 50,0 | 70,4 ± 4,9 |
|  | 25,0 | 33,7 ± 2,1 |
|  | 12,5 | 18,4 ± 10,5 |

Tables 21 and 22 (reported in the following) further show the results of tests showing the effect of MED15 on $TXB_2$ (thromboxane) plasma levels in the rat compared with that of ASA and controls and the kinetics of percentage inhibition of $TXB_2$ plasma levels in the rat, respectively.

TABLE 21

Effect of MED 15 and of ASA on $TXB_2$ plasma levels in the rat

| Groups | $TXB_2$ ng/ml ± S.E. | % of inhibition | P |
|---|---|---|---|
| Controls | 174.1 ± 42.6 | — | — |
| ASA | 2.9 ± 1.1 | 98.3 | 0.003 |
| MED 15 | 14.3 ± 1.3 | 91.8 | 0.004 |

TABLE 22

Kinetics of percentage inhibition of $TXB_2$ plasma levels in the rat

| Groups | % of inhibition | P |
|---|---|---|
| Controls | — | — |
| MED 15 |  |  |
| 0.75 h | 93.2 | 0.0001 |
| 1.5 h | 90.8 | 0.0001 |
| 3.0 h | 91.4 | 0.0001 |
| 6.0 h | 93.7 | 0.0001 |
| 24.0 h | 49.2 | 0.032 |

This effect is prolonged, covering a span of 24 hours. The above show that MED 15 does possess inhibitory effects on blood platelet aggregation.

In view of the above properties and of the additional lack of gastrolesive effects, MED 15 may be used to counteract the platelet aggregation in patients in need of such a treatment and who are intolerant to acetyl salycylic acid and, in general, to NSAIDs, advantageously when such treatment has to be carried out for a long time. As clarified in connection with the action mechanism, in order to exert its gastroprotective effects MED 15 has to be administered on empty stomach and without a simultaneous assumption of anti-$H_1$ substances.

It is therefore an object of the present invention a method for counteracting blood platelet aggregation in patients in need thereof and intolerant to acetyl salicylic acid and to NSAIDs, comprising administering on empty stomach and without a simultaneous assumption of anti-$H_1$-substances an amount of 2-metoxyphenyl-1-metyl-5p-methylbenzoyl-pyrrol-2 acetamido acetate effective to counteract blood platelet aggregation.

The dosage of administration of MED 15 to show its anti-aggregating property ranges from 300 to 600 mg/day; the drug may be administered alone or together with usual pharmaceutically tolerable vehicles as pharmaceutical compositions.

Effect of MED 15 on thrombophlebitis.

MED 15 may be also used in the treatment of thrombophlebitis, in particular in case of thrombophlebitis of women who have just given birth.

In general a thrombophlebitis may be defined as an inflammation of a vein associated with the formation of a thrombus or clot. In that case around the clot in a vascular bed there is a peculiar situation, which provokes simultaneously pain and inflammation. In order to treat the patient suffering from thrombophlebitis both pain and inflammation have to be treated simultaneously. Among the drugs most frequently used are NSAIDs, for their specific capability of treating pain and inflammation, that is to say their anti-inflammatory and antalgic properties(see bibliographic references No.44–46). However the simple use of a NSAID, at least of one of the NSAIDs known from the state of art, may not be regarded as sufficient in order to treat completely a thrombophlebitis. As a matter of fact and at the same time, there is also the need of a thrombolytic effect, which is normally carried out by administering a streptokinase or urokinaase or a tissue plasminogen activator (tPA). Moreover, to enhance the possibility of liberating the vessel from the clot it would extremely useful to exert locally a vasodilating effect. This vasodilating effect by enlarging the section of the vessel facilitates the liberation of the clot from the vessel. Finally, once the vessel is freed from the clot, there is the further need of avoiding the occurrence of similar pathological conditions, which can be realised by using antiaggregating substances in order to avoid platelet sticking into the vessels. The substances commonly used to this purpose are aspirin, heparin and low molecular weight heparinoids.

In view of what above stated and to sum up, it appears clear that in order to treat a thrombophlebitis five goals have to be reached: treatment of pain and inflammation, vasodilation, thrombolisis of the clot and avoidance of platelet sticking. From the state of the art the above can be accomplished by using at least four kinds of drugs: a NSAID (for pain and inflammation), an aspirin or a heparin-like substance (antiaggregation), a urokinase-like substance (thrombolitic effect) and a vasodilating substance. Additionally, since the most frequently used drugs for the treatment of pain and inflammation are NSAIDs, which are known to be gastrolesive and to which many patients are intolerant (or easily develop an intolerance after a prolonged treatment), it will be also necessary to administer a gastroprotective drug, such as a protonic pump inhibitor like omprazole or an anti-$H_2$ substance like famotidine. Therefore a substance simultaneously showing antalgic and antinflammatory properties as well as platelet antiaggregating and vasodilating effect would be extremely useful.

The platelet anti-aggregating properties of MED 15 have been shown before.

The effect of vasodilation of MED 15 has been shown before with reference to the mechanism of action. To sum up it may be stated that the administration of MED15 provokes in the stomach the production of CGRP with subsequent outflow of the peptide into the bloodstream and the possibility of reaching various organs. The vasodilating action of CGRP also depends on NO formation, which functions as second messenger of the CGRP-induced vasodilation. Therefore, the effect of vasodilation provoked by CGRP, and consequently by NO, takes place in each organ reached. This effect of CGRP is evident in human coronary artery dilation (see bibliographic references No.47–51). In this respect what has to be stressed is that while the vasodilating effect of CGRP and NO per se may be regarded as known from the literature, it is not known at all the fact that CGRP is produced by the action mechanism of MED 15.

A final consideration in using MED 15, as NSAID for its anti-inflammatory and antalgic properties is that MED 15 shows a gastroprotective effect not shown by any other NSAID. These facts, which again may be explained by the action mechanism, has the further advantage that; gastroprotective drugs such as a protonic pump inhibitor, like omeprazole or an anti-$H_2$ substance like famotidine, have not to be simultaneously administered. The gastroprotective effect of MED 15 gives the possibility of administering it safely and for a long term in puerperium or in pathological conditions when a cronic risk of thrombophlebitis is in act. The administration of MED 15 has to take place on an empty stomach and without a simultaneous assumption of anti-$H_1$ substances.

Consequently, the use of only one drug, MED15, allows the treatment of the following factors which have to be dealt with in case of a thrombophlebitis, namely pain and inflammation, vasodilation and avoidance of the sticking of platelets. In addition, in view of the gastroprotective properties of MED 15, it is possible to avoid the assumption of a further gastroprotective drug.

It is therefore an object of the present invention a method for treating thrombophlebitis, particularly in case of puerperium, comprising administering to a patient in need thereof on an empty stomach and without a simultaneous assumption of anti-$H_1$ substances an amount of 2-methoxyphenyl-1-methyl-5p-methylbenzoyl-pyrrol-2-acetamido acetate effective to treat pain and inflammation, to exert local vasodilation, to avoid platelet sticking and to protect the stomach from NSAID-related gastric damages.

The dosage of administration of MED 15 ranges from 600 to 1200 mg/day; the drug has to be administered on an empty stomach and without a simultaneous assumption of anti-$H_1$ substances alone or together with usual pharmaceutically tolerable vehicles as pharmaceutical composition.

Vasodilating properties of MED15.

MED 15 may also be used in the treatment of other patients thanks to its vasodilating properties connected with the liberation in the blood stream of CGRP. The main use of MED 15, as for any NSAID, is for the treatment of pain and inflammation; however, the unexpected properties due to its action mechanism, make it possible to administer MED15 with advantageous effects to patients which benefit of a vasodilating effect in addition to the antinflammatory and antalgic properties. The treatment with MED15 may be useful for patients, who need a treatment with a NSAID, namely an antinflammatory and an antalgic treatment, and at the same time are infarct patients. This may be explained taking into account that it is well known that MED 15 produces CGRP, which in turn is known to produce vasodilation also through release of NO; in case of infarct patients the vasodilation would act on the coronary arteries with a beneficial effect on the patient.

It is therefore a further object of the present invention a method for treating pain and inflammation in an infarct patient comprising administering on an empty stomach and without a simultaneous assumption of anit-$H_1$ substances an amount of 2-methoxyphenyl-1-methyl-5p-methylbenzoyl-pyrrol-2-acetamido acetate effective to treat pain and inflammation and to exert a vasodilatative effect on coronary arteries.

A further class of patients who may be treated with MED15 thanks to its vasodilating properties is the class of patients who suffered or are under the risk of a stroke of the cerebral vessels. To clarify the possibility of treatment with MED-15 of this new class of patients a distinction has to be drawn between the two basic kinds of cerebral stroke. A cerebral stroke may be generally defined as a discontinuity of a cerebral vessel. This discontinuity may have two origins: a thrombotic origin (that is to say the vessel becomes obstructed by a thrombus) and an haemorragic origin (that is to say the vessel breaks). The strokes having thrombotic origin are treated with antiaggregating substances, while those having an haemorragic origin are treated with antihaemorragic substances. The two treatments are therefore opposite. MED 15 may be used in the treatment of patients suffering from a cerebral stroke of thrombotic origin who need an antinflammatory and an antalgic treatment and are intolerant to NSAIDs. The vasodilating effect on the cerebral vessels is beneficial the patients. The administration has to take place on an empty stomach and without a simultaneous assumption of anti-$H_1$ substances.

It is therefore a further object of the present invention a method for treating pain and inflammation in patient affected by or under the risk of cerebral stroke of thrombotic origin comprising administering on empty stomach and without a simultaneous assumption of anti-$H_1$ substances an amount of 2-methoxyphenyl-1-methyl-5p-methylbenzoyl-pyrrol-2-acetamido acetate effective to treat pain and inflammation and to exert a vasodilating effect on the cerebral vessels.

The dosage of administration of MED 15 ranges from 600 to 1200 mg/day; the drug may be administerd alone or together with usual pharmaceutically tolerable vehicles as pharmaceutical composition.

BIBLIOGRAPHY

1) Matera Prof. M., 1st. di Farmacologia, Cattedra di Chemioterapia, Facolta di Medicina e Chirursia, Universita di Catania, 1986, "Evaluation of the pharmacodynamic activity of MED 15—antinflammatory, analgesic and antipyretic activity".

2) Seed M. P., Greenslade K. J., Willoughby D. A., William Harvey Research Inst., London, 1996, "Study into the EFiects of MED15 on Monoarticular Arthritis in the Rat".

3) Greenslade K. J., Moore A. R., Willoughby D. A., William Harvey Research Inst., London, 1996, "Study into the Effects of MED15 on Carrageenan Pleurisy in the Rat".

4) Matera Prof. 1st. di Farimacologia, Cattedra di Chemioterapia, Facolta di Medicina e Chirurgia, Universita di Catania, 1989, "Effects of MED 15 on Blood Pressure, ECG and Hearbeat Frequency in the Anaesthetized Rat".

5) Matera Prof M., 1st. di Farmacologia, Cattedra di Chemioterapia, Facolta di Medicina e Chirurgia, Universita di Catania, 1989, "Study of the Acute Toxicity of MED15".

6) Zühlke U., Hazleton Research Labs., 1992, Project 419–500, "Medosan15–52-week oral (gavage) chronic toxicity study in the rat with an eight-week treatment-free period".

7) Zühlke U., Hazleton Research Labs, Project 419–501, 1992, "Medosan15–52-week oral (gavage) chronic toxicity study in the cynomolgous monkey with an eight-week treatment-free period".

8) Allen P. A., Mladenovic P., Terrier Ch., RCC Research % Consulting Company, 1989, "Embryotoxicity Study (Including Teratogenicity) with MED15 in the Rat and in the Rat".

9) Allen P. A., Mladenovic P., Terrier Ch., RCC Research % Consulting Company, 1989, "Emnbryotoxicity Study (Including Teratogenicity) with MED15 in the Rat and in the Rabbit".

10) Allen P. A., Miladenovic P., RCC Research & Consulting Company, 1989, "Fertility and General Reproduction Study with MED15 in the Rat".

11) Forster R., Monaco M., Nunziata A. LSR-RTC, 1983, "Reverse Mutation in Salmonella Typhimurium. Test substance: Medosan15 (Ames Test)".

12) Forster R., Monaco M., Nunziata A., LSR-RTC, 1933, "Forward Mutation in Schizosaccharomyces Pombe 1. Test substance: Medosan15".

13) Forster R., Monaco M., Nunziata A., LSR-RTC, 1983, "Mitotic Gene Conversion in Saccharomyces Cerevisiae D4. Test substance: Medosan15".

14) Conz A., Fumero S., RBM Antione Marxer, 1989, "Chromosome Aberrations in Human Lymphocytes Cultured in vitro. Test substance: MED15".

15) Conz A., Fumero S., RBM Antione Marxer, 1989, "Micronucleus Test in Rat Bone Marrow Test substance: MED15".

16) Germano O., Maraschin R., RBM Antione Marxer, 1995, "Evaluation of the carcinogenicity of the test article ST679/MED15 administered by oral route to the rat for a period covering most of its lifespan".

17) Tubaro. E., Belogi L., Mezzadri C. M., Ruco L., Stoppacciaro A. "Studies on the gastric tolerability of the new non-steroidal anti-inflammatory drug amtolmetin guacyl". Arzneim Forsch Drug Res 1995;45:1298–1302.

18) Bunce K. T., Parsons M. E. "A quantitative study of medamide, a histamine $H_2$-antagonist, on the isolated whole rat stomach" J Physiol 1976; 258:453–465, 19) Boughton-Smith N. K., Whirtle B. J. R. "The gastric antisecretory actions of prostaglandin $E_2$ and stable prostacyclin analogues against different secretagogues in perfused whole stomachs of rat of mouse in vitro" Br J Pharmacol 1931;72:291–298.

20) Wan B. Y. C. "Metiamide and stimulated acid secretion from the isolated non-distended and distended mouse stomach" J Physiol 1977;266:327–346.

21) Suzuki A., Kamejama J., Tsukamoto M., Suzuki Y. "Bicarbonate secretion in isolated guinea-pig antrum" J Clin Gastroenterol, 1990;12(Suppl):14–18.

22) Kameyama J., Suzuki A., Tsukamoto M., Suzuki Y., Kaneko K. "Effects of bile acids and bilirubin on bicarbonate secretion of isolated guinea-pig antrum" J Clin Gastroenterol, 1992;14(Suppl): 102–106.

23) Leithold M., Fleissig W., Merk A. "Anti-ulcer and secretion-inhibitory properties of the tricyciic derivative Doxepin in rats and dogs". Arzneim Forsch Drug Res. 1984;34:468–473.

24) Munt P. I., Williams C. Huntingdon Life Sciences U. K., 1996 "MED15 (amtolmetine guacyl)—Effect on gastric acid secretion in the anaesthetized rat".

25) Munt P. I., Williams C. Huntingdon Life Sciences U. K., 1996"MED15 (amtolmetine guacyl)—Effect on gastric acid secretion in vitro".

26) Bertaccini G., Coruzzi G., Scarpignato C. "Effects of alkyl analogues of histamine and metiamide on the isolated guinea pig heart". Pharmacology 1981;22:101–107.

27) Odes H. S., Hogan D. L., Steinbach H. H., Ballesteros M. A., Koss M. A., Isenberg J. I. "Measurement of gastric bicarbonate secretion in the human stomach: different methods produce discordant results " Scand J Gastroenterol 1992;27:829–836.

28) Segawaa K., Arisawa T., Niwa Y. Kato T., Tsukamoto Y., Goto H., Hayakawa T., Nakazawa S. "The relationship between titrated acidity (m.Eq/1) and pH of human gastric juice: a study based on the data estimated by pHmeter". Nippon Shokakibyo Gakkai Zasshi 1994;91:849–853.

29) Barker L. A. "Histamine HI and muscarinic receptor antagonist activity of cimetidine and tiotidine in the guinea pig isolated ileum". Agents Actions 1981;11:699–705

30) Vane J. "A sensitive method for the assay of 5H-hydroxytryptamine". Br J Pharmac 1957;12:344–349.

31) Manela F. D., Ren J., Gao J., McGuigan J. E., Harty R. F. "Calcitonin gene-related peptide modulates acid-mediated reguation of somatostatin and gasatrin release from rat antrum" Gastroenterology 1995;109:701–706.

32) Ren J., Young R. L., Lassiter D. C., Harty R. F. "Calcitonin gene-related peptide mediates capsaicin-induced neuroendocrine responses in rat antrum" Gastroenterology 1993;104:485–491.

33) Takeuchi K., Ohuchi T., Matsumoto J., Okabe S. "Regulation of gastroduodenal bicarbonate secretion by capsaicin-sensitive sensory neurons in rats". J Clin Gastroenterol 1993;17(Suppl):533–539.

34) Yeh J. L., Le Y. C., Wang Y., Chen I. J. "Cardiovascular interactions of nonivamnide, glyceryl nonivamide, capsaicin analogues, and substance P antagonist in rats". Brain Res Bull 1993;30:641–648.

35) Wu P. C., Fang J. Y., Huang Y. B., Tsai Y. H. "In vitro effect of penetration enhancers on sodium nonivamide acetate in rat skin". Biol Pharm Bull 1995;18:1790–1792.

36) WU J. R, Fann S. F., Yeh J. L., Lo Y. C., Huang T. Y., Chen I. J. "Multiple sensory and functional effects of non-phenolic aminodimethylene nonivamide: an approach to capsaicin antagonist". Gen Pharnacol 1996,27;151–158.

37) Mathison R, Davison J. S. "Regulation of jejunal arterioles by capsaicin-sensitive nerves in Nippostrongylus brasiliensis-sensitized rats". J Pharmacol Exp Ther 1995;273:337–343.

33) Wallace J. L., McKnight G. W., Befus A. D. "Capsaicin-induced hyperemia in the stomach: possible contribution of mast cells". Am J Physiol 1992;263:G209–14.
39) Palla R., Parrini M., Panichi V., Andreini B., De Pietro S. "Acute effects of calcitonin gene related peptide on renal haemodynamics and renin and angiotensin II secretion in patients with renal disease". Int J Tissue React 1995;17:43–49.
40) Tache Y., Raybould Y., Wei J. Y. "Central and peripheral actions of calcitonin gene related peptide on gastric secretory and motor function". Adv Exp Med Biol 1991;298:183–193.
41) Lamrecht N., Burchert M., Respondek M., Muller K. M., Peskar B. M. "Role of CGRP and NO in the gastroprotective effect of capsaicin in the rat". Gastroenterology 1993; 104:1371–1380.
42) Kline L. W., Pang P. K. T. "Nitric oxide modulates the CGRP-induced relaxation in guinea pig gallbladder strips in vitro". Rag Pept 1994; 50:207–212.
43) Garcia G. E., Hammond T. C., Wead L. M., Mendonca M. M., Brown N. R., Gabbai F. B. "Effect of angiotensin II on the renal response to aminoacid in rats". Am J Kidney Dis 1996; 1:115–23.
44) Berrazueta J. R., Poveda J. J., Ochoteco J., Amado J. A., Puebla F., Salas E., Sarabia M. "The anti-inflammatory and analgesic action of transdermal glyceryltrinitrate in the treatment of infusion-related thrombophlebitis". Postgrad Med J 1993; 69:37–40.
45) Berrazueta J. R., Fleitas M., Salas E., Amado J. A., Poveda J. J., Ochoteco J., Sanchez de Vega M. J., Ruiz. de Celis G. "Local transdermal glyceryltrinitrate has an anti-inflammatory action on thrombophlebitis-induced be sclerosis of leg varicose veins". Angiology 1994; 45:347–351.
46) Ridker P. M., Cushman M., Stampfer M. J., Tracy R. P., Hennekens C. H. "Inflammation, aspirin, and the risk of cardiovascular disease in apparently healthy men". N Engl J Med 1997; 336:973–979.
47) Franco-Cereceda A., Rudehill A. "Capsaicin-induced vasodilation of human coronary arteries in vitro is mediated by calcitonin gene-related peptide rather than substance P or neurokinin A". Acta Physiol Scand 1989; 136:575–580.
48) Franco-Cereceda A. "Calcitonin gene-related peptide and human epicardial coronary arteries: presence, release and vasodilator effects". Br J Pharmacol 1991; 102:506–10.
49) Bell D., McDermott B. J. "Inhibition by verapamil and diltiazem of agonist-stimulated contractile responses in mammalian cardiomyocytes". J Mol Cell Cardiol 1995; 27:1977–87.
50) Quebbeman B. B., Dulas D., Altman J., Homans D. C., Bache R. J. "Effect of calcitonin gene-related peptide on well-developed canine coronary collateral vasculature". J Cardiovasc Pharmacol 1993; 21:774–80.
51) Ohmura T., Nishio M., Kigoshi S., Muramatsu I. "Electrophysiological and mechanical effects of calcitonin gene-related peptide on guinea-pig atria". Br J Pharmacol 1990; 100:37–30.
52) Bjarnason I., Hayllar J., MacPherson A. J., Russell A. S. "Side effects of nonsteroidal anti-inflammatory drugs on the small and large-intestine in humans". Gastroenterology 1993 Jun; 104(6):1832–1847

What is claimed is:

1. A method for counteracting blood platelet aggregation over a short or long term in a patient in need thereof and who is intolerant to acetyl salicylic acid and to non-steroidal anti-inflammatory drugs (NSAIDS), comprising administering to a patient in need thereof on an empty stomach and without a simultaneous administration of antihistamine substances, an amount of 2-methoxyphenyl-1-methyl-5 p-methylbenzoyl-pyrrol-2 acetamido acetate effective to counteract blood platelet aggregation.

2. The method according to claim 1, wherein 2-methoxyphenyl-1-methyl-5 p-methylbenzoyl-pyrrol-2-acetamido acetate is administered in a dosage ranging from 300 to 600 mg/day.

3. The method according to claim 2, wherein 2-methoxyphenyl-1-methyl-5 p-methylbenzoyl-pyrrol-2-acetamido acetate is administered together with usual pharmaceutically tolerable vehicles.

4. A method for treating thrombophlebitis, comprising administering to a patient in need thereof on an empty stomach and without a simultaneous administration of antihistamine substances an amount of 2-methoxyphenyl-1-methyl-5 p-methylbenzoyl-pyrrol-2-acetamido acetate effective to exert local vasodilation, to avoid platelet sticking and to protect the stomach from NSAID-related gastric damages.

5. The method according to claim 4, wherein said patient is suffering from thrombophlebitis derived from puerperium.

6. The method according to claim 5, wherein 2-methoxyphenyl-1-methyl-5 p-methylbenzoyl-pyrrol-2-acetamido acetate is administered in a dosage ranging from 600 to 1200 mg/day.

7. The method according to claim 6, wherein 2-methoxyphenyl-1-methyl-5 p-methylbenzoyl-pyrrol-2-acetamido acetate is administered together with at least one usual pharmaceutically tolerable vehicle.

8. The method of claim 4 wherein said amount is an amount also effective to treat pain and inflammation.

9. A method for treating an infarct patient comprising administering to said infarct patient on an empty stomach and without a simultaneous administration of antihistamine substances an amount of 2-methoxyphenyl-1-methyl-5 p-methylbenzoyl-pyrrol-2-acetamido acetate effective to exert a vasodilating effect on coronary arteries.

10. The method according to claim 9, wherein 2-methoxyphenyl-1-methyl-5 p-methylbenzoyl-pyrrol-2-acetamido acetate is administered in a dosage ranging from 600 to 1200 mg/day.

11. The method of claim 9 wherein said amount is an amount also effective to treat pain and inflammation.

12. A method for treating a patient affected by or under the risk of cerebral stroke of thrombotic origin comprising administering to said patient on an empty stomach and without a simultaneous administration of antihistamine substances an amount of 2-methoxyphenyl-1-methyl-5 p-methylbenzoyl-pyrrol-2-acetamido acetate effective to exert a vasodilating effect on cerebral vessels.

13. The method according to claim 12, wherein 2-methoxyphenyl-1-methyl-5 p-methylbenzoyl-pyrrol-2-acetamido acetate is administered in a dosage ranging from 600 to 1200 mg/day.

14. The method of claim 12 wherein said amount is an amount also effective to treat pain and inflammation.

* * * * *